(12) United States Patent
Yun et al.

(10) Patent No.: US 10,864,283 B2
(45) Date of Patent: Dec. 15, 2020

(54) COMPOSITION FOR PREVENTING OR TREATING KELOID OR HYPERTROPHIC SCARS

(71) Applicant: INDUSTRY-UNIVERSITY COOPERATION FOUNDATION HANYANG UNIVERSITY, Seoul (KR)

(72) Inventors: Chae Ok Yun, Seoul (KR); Won Jai Lee, Seoul (KR)

(73) Assignee: INDUSTRY-UNIVERSITY COOPERATION FOUNDATION, HANYANG UNIVERSITY

(*) Notice: Subject to any disclaimer, the term of this patent is extended or adjusted under 35 U.S.C. 154(b) by 134 days.

(21) Appl. No.: 16/028,283

(22) Filed: Jul. 5, 2018

(65) Prior Publication Data

US 2018/0326094 A1 Nov. 15, 2018

Related U.S. Application Data

(63) Continuation-in-part of application No. PCT/KR2017/000154, filed on Jan. 5, 2017.

(30) Foreign Application Priority Data

Jan. 5, 2016 (KR) .................. 10-2016-0001031

(51) Int. Cl.
| | |
|---|---|
| C12N 15/113 | (2010.01) |
| A61K 48/00 | (2006.01) |
| G01N 33/50 | (2006.01) |
| A61K 39/00 | (2006.01) |
| A61K 39/395 | (2006.01) |
| A61K 39/235 | (2006.01) |
| A61P 17/02 | (2006.01) |
| C12N 15/861 | (2006.01) |

(52) U.S. Cl.
CPC .......... *A61K 48/0066* (2013.01); *A61K 39/00* (2013.01); *A61K 39/235* (2013.01); *A61K 39/395* (2013.01); *A61K 48/00* (2013.01); *A61P 17/02* (2018.01); *C12N 15/113* (2013.01); *C12N 15/861* (2013.01); *G01N 33/50* (2013.01); *C12N 2310/11* (2013.01); *C12N 2310/14* (2013.01); *C12N 2310/141* (2013.01); *C12N 2310/531* (2013.01)

(58) Field of Classification Search
CPC ... C12N 15/111; C12N 15/113; C12N 15/861; C12N 2310/14
See application file for complete search history.

(56) References Cited

U.S. PATENT DOCUMENTS

2012/0302729 A1* 11/2012 Wadhwa .................. A61P 37/04
530/328

FOREIGN PATENT DOCUMENTS

| EP | 3400966 A1 * | 11/2018 | ............ A61K 48/00 |
|---|---|---|---|
| JP | 2006-089471 | 4/2006 | |
| KR | 10-2010-0066429 | 6/2010 | |
| WO | WO-2017119744 A1 * | 7/2017 | ............ G01N 33/50 |
| WO | WO-2017173237 A1 * | 10/2017 | ............... C12Q 1/68 |

OTHER PUBLICATIONS

Yoo et al. (Journal of Gene Medicine (2010) vol. 12(7):586-595). (Year: 2010).*
Translation of WO2017/119744 retrieved from https://patentscope.wipo.int on Aug. 3, 2020 (Year: 2020).*
Ladin et al., "p53 and apoptosis alterations in keloids and keloid fibroblasts", Wound Rep Reg 1998; 6:28-37.
Lee et al., "Adenovirus-relaxin gene therapy for keloids: implication for reversing pathological fibrosis", British Journal of Dermatology, 2011, v. 165, pp: 673-677.
Lee et al., "Proteomic Profiling Reveals Upregulated Protein Expression of Hsp70 in Keloids", Hindawi Publishing Corporation, BioMed Research International, vol. 2013, Article ID 621538, 9 pages, http://dx.doi.org/10.1155/2013/621538.
Office Action issued for KR 10-2016-0001031, dated Oct. 23, 2018, 6 pages.
Gispert et al., "Loss of mitochondrial peptidase Clpp leads to infertility, hearing loss plus growth retardation via accumulation of CLPX, mtDNA and inflammatory factors", Human Molecular Genetics, 2013, vol. 22, No. 24:4871-4887.
Ladin et al., "p53 and apoptosis alterations in keloids and keloid fibroblasts", Wound Repair and Regeneraton, vol. 6, No. 1: 28-37, Jan. 1998.
Lee et al., "Proteomic Profiling Reveals Upregulated Protein Expression of Hsp70 in Keloids", BioMed Research International, vol. 2013, 9 pages.
Ahn et al., "Inhibition of Mortalin leads to anti-fibrosis and apoptosis of the keloid spheroid", Molecular Therapy, vol. 26, No. 5, May 2018, XP-002793125.
European Search Report—Supplementary—for EP 17736116.9, dated Aug. 5, 2019, 9 pages.
Jurzak et al., "Evaluation of Genistein Ability to Modulate CTGF mRNA/Protein expression, Genes Expression of TGFβ Isoforms and Expression of Selected Genes Regulating Cell Cycle in Keloid Fibroblasts In Vitro", Acta Poloniae Pharmaceutica—Drug Research, vol. 71, No. 6., pp. 972-986, 2014.
Lee et al., "Mortalin deficiency suppresses fibrosis and induces apoptosis in keloid spheroids", Scientific Reports, vol. 7, 10 pages, Oct. 2017.

(Continued)

*Primary Examiner* — J. E Angell
(74) *Attorney, Agent, or Firm* — Adsero IP

(57) ABSTRACT

The present invention relates to a pharmaceutical composition for preventing or treating a keloid disease or scars. The inventors of the present invention discovered that mortalin expression inhibition and the interaction between mortalin and p53 may be new targets for keloid treatment. In the present invention, apoptosis and an anti-fibrotic effect were verified by preparing a mortalin-specific shRNA (dE1-RGD/GFP/shMOT) and injecting same in a keloid spheroid. Thus, by reducing ECM expression and inducing apoptosis in a keloid spheroid, mortalin knockdown may be very usefully employed for keloid treatment.

8 Claims, 15 Drawing Sheets
Specification includes a Sequence Listing.

(56) References Cited

OTHER PUBLICATIONS

Liu et al., "Mesenchymal stem cell-mediated suppression of hypertrophic scarring is p53 dependent in a rabbit ear model", Stem Cell Research & Therapy, 2014, vol. 5, 10 pages.
Tanaka et al., "Expression of p53 family in scars", Journal of Dermatological Science (2004) 34, 17-24.

* cited by examiner

[FIG. 1A]
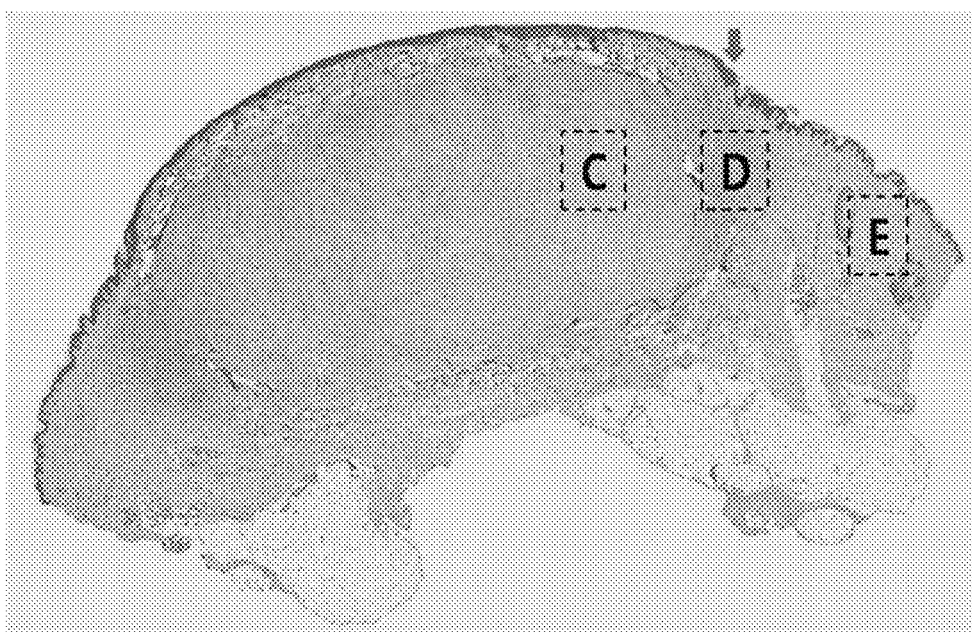
[FIG. 1B]
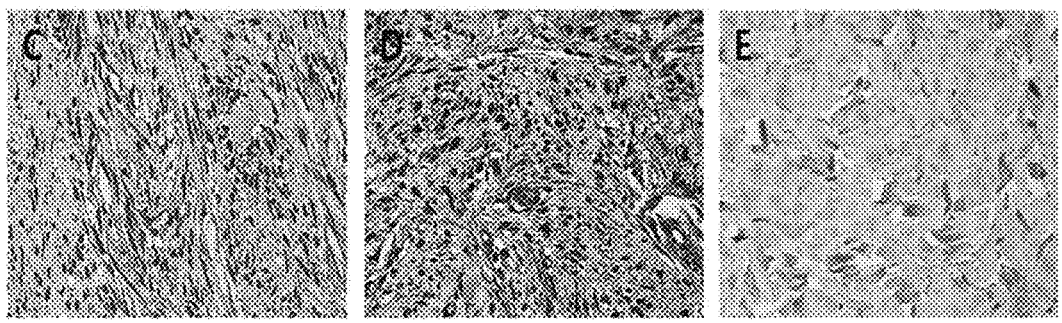

[FIG. 1C]
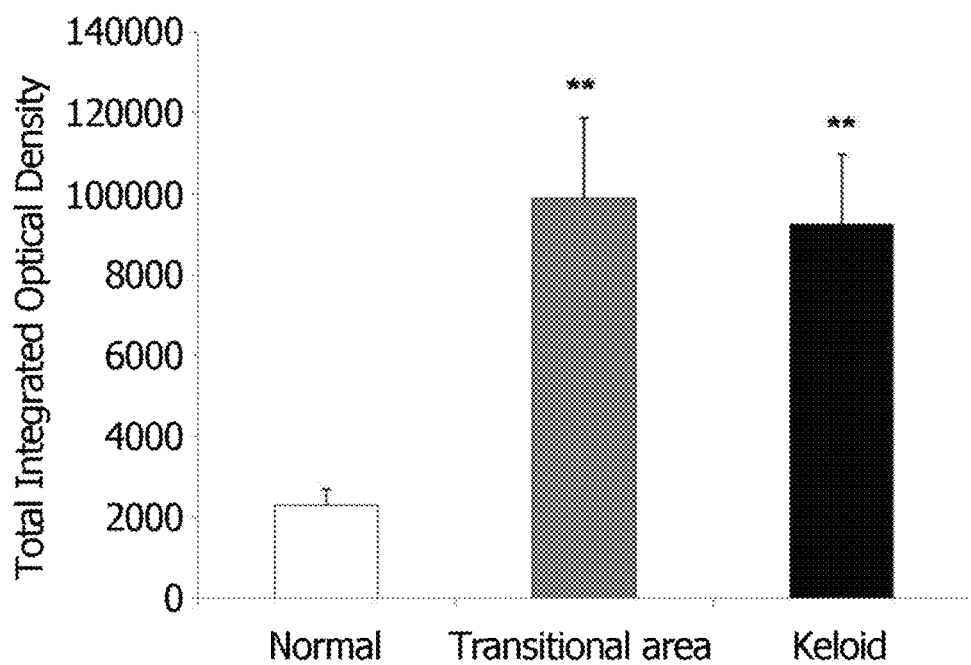
[FIG. 2A]
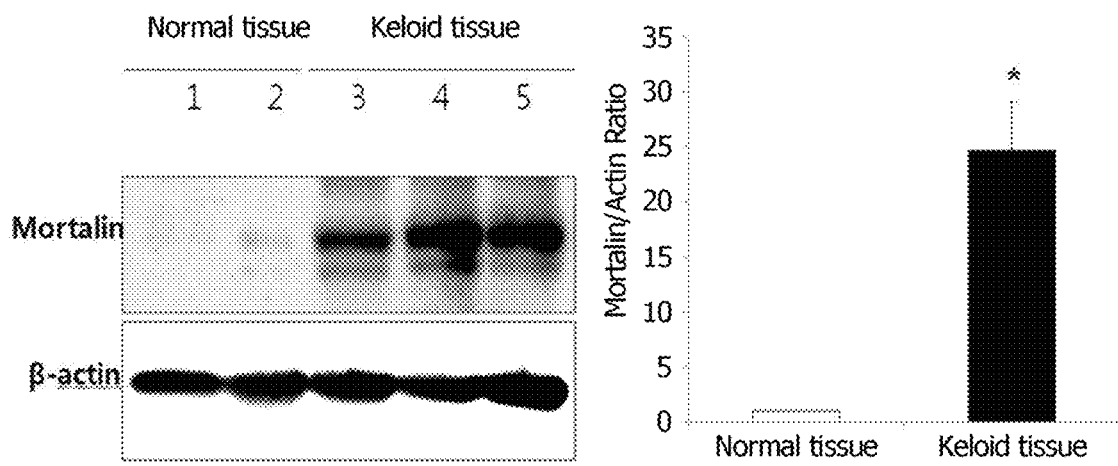

[FIG. 2B]
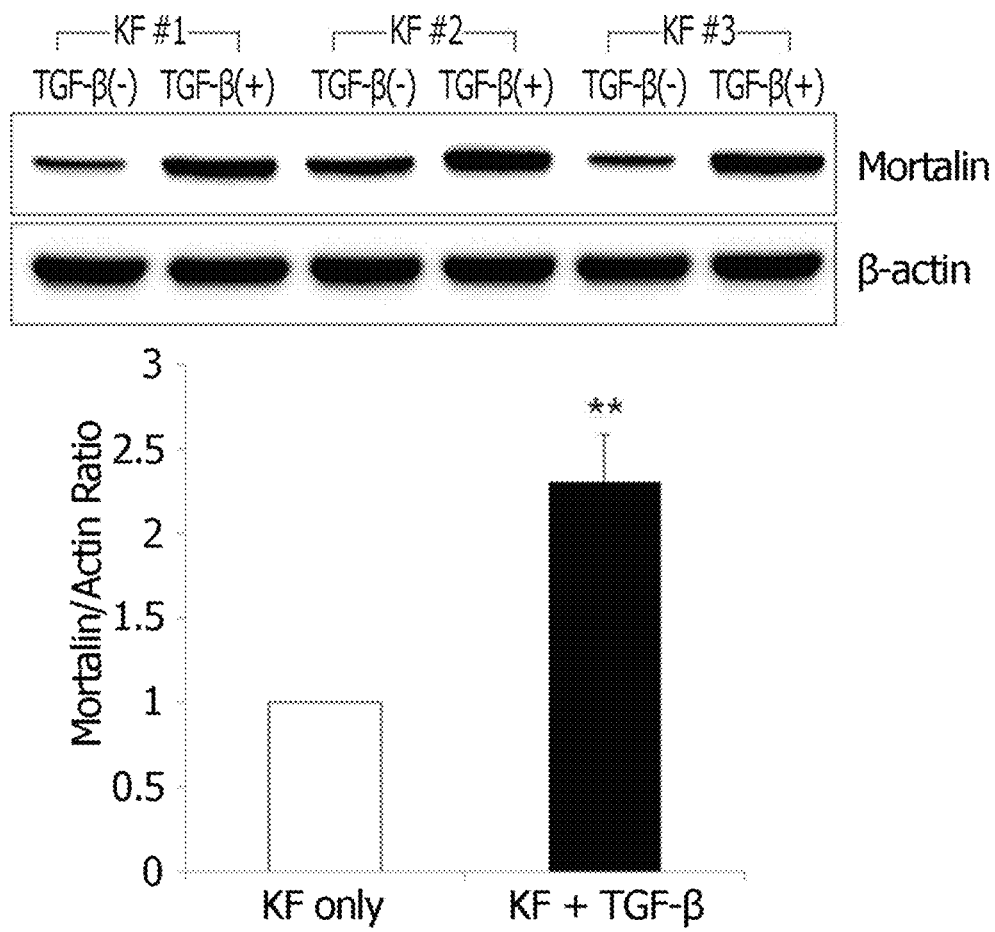
[FIG. 3A]
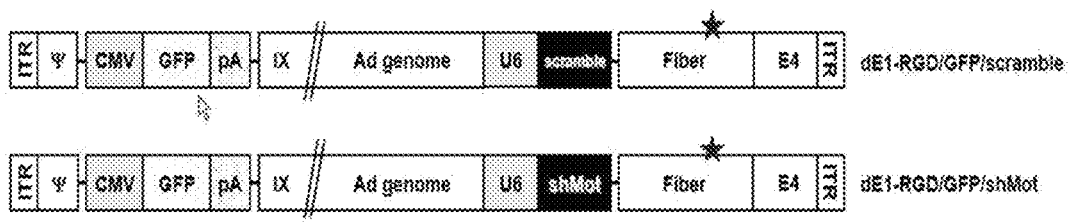

[FIG. 3B]
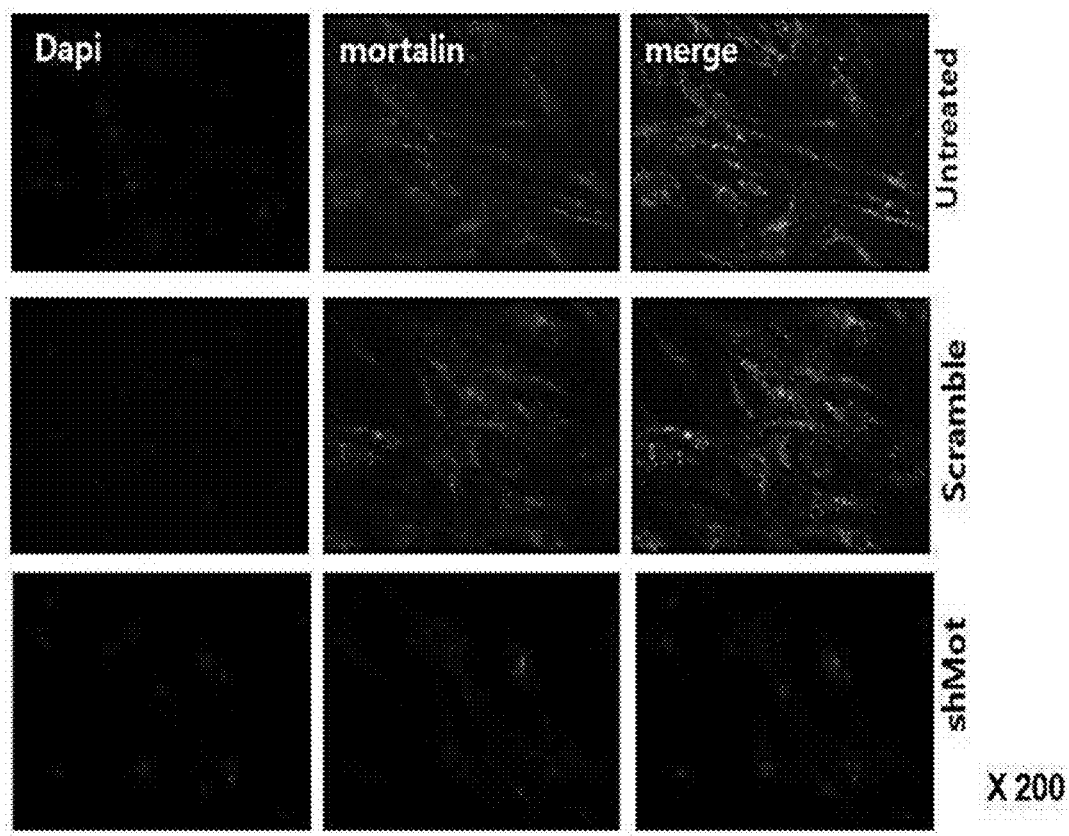

[FIG. 3C]
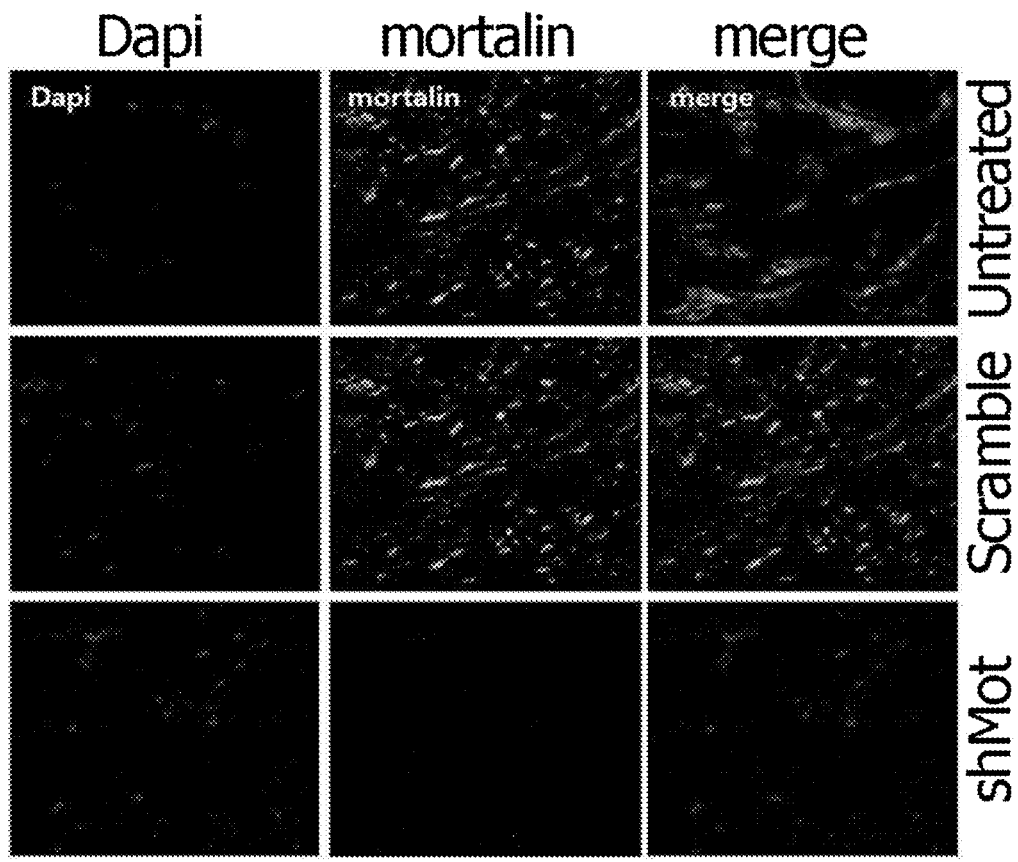
[FIG. 4A]
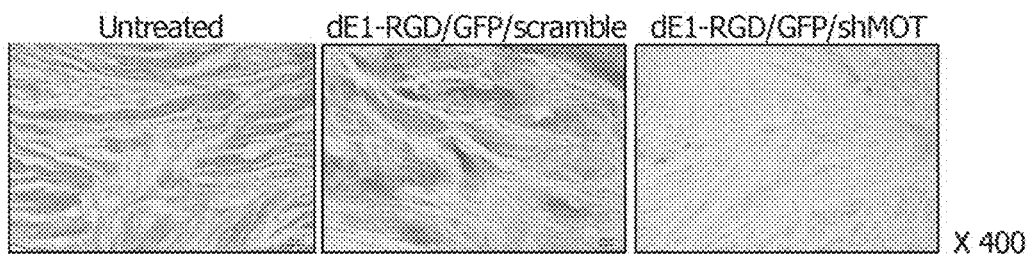

[FIG. 4B]
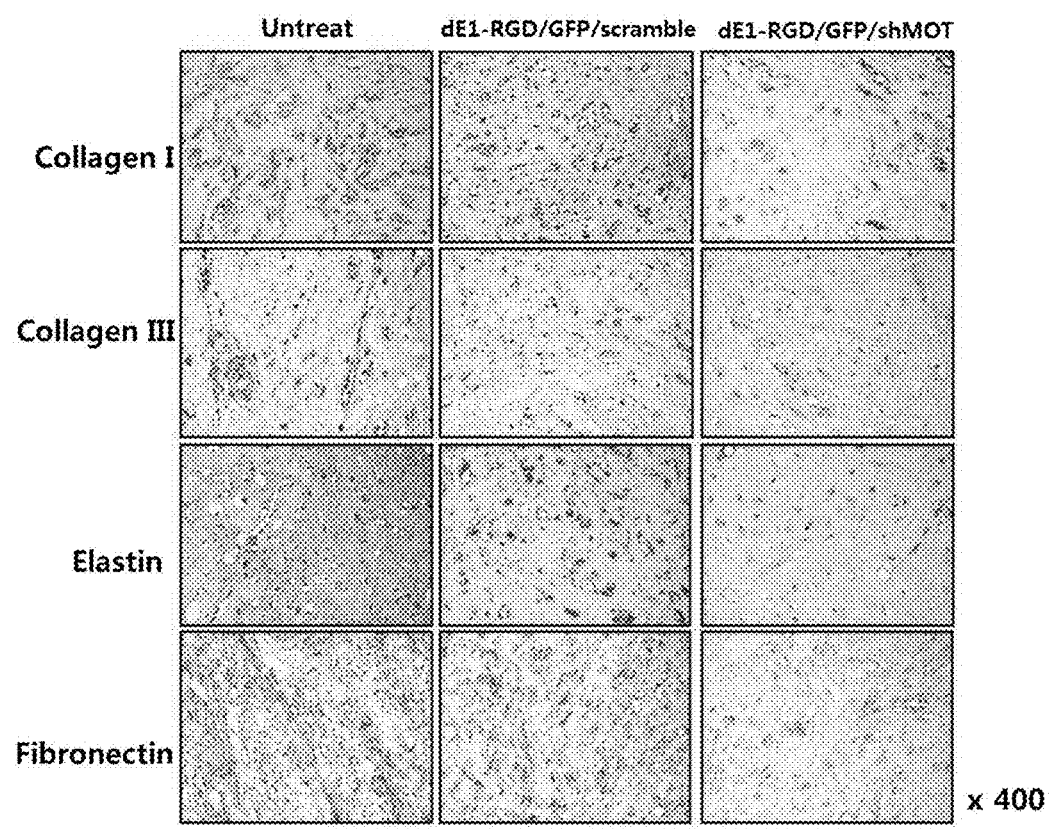

[FIG. 4C]
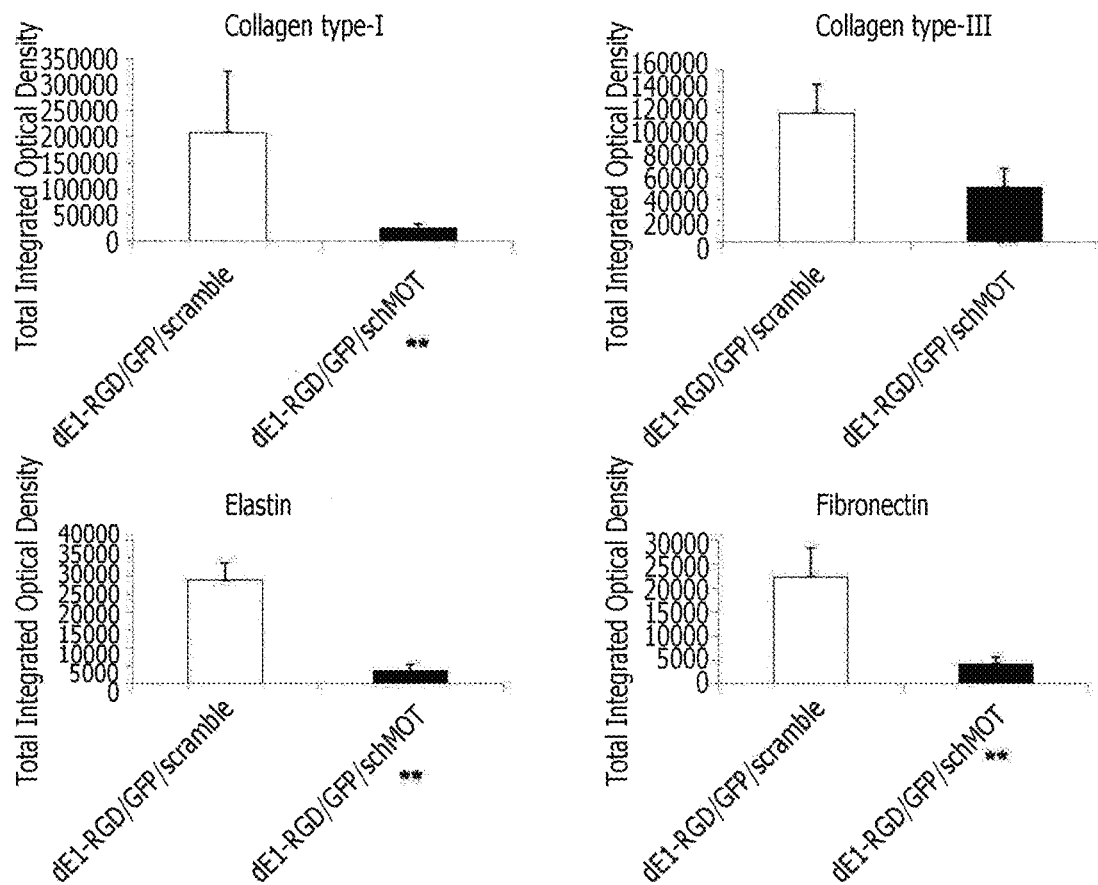

[FIG. 4D]
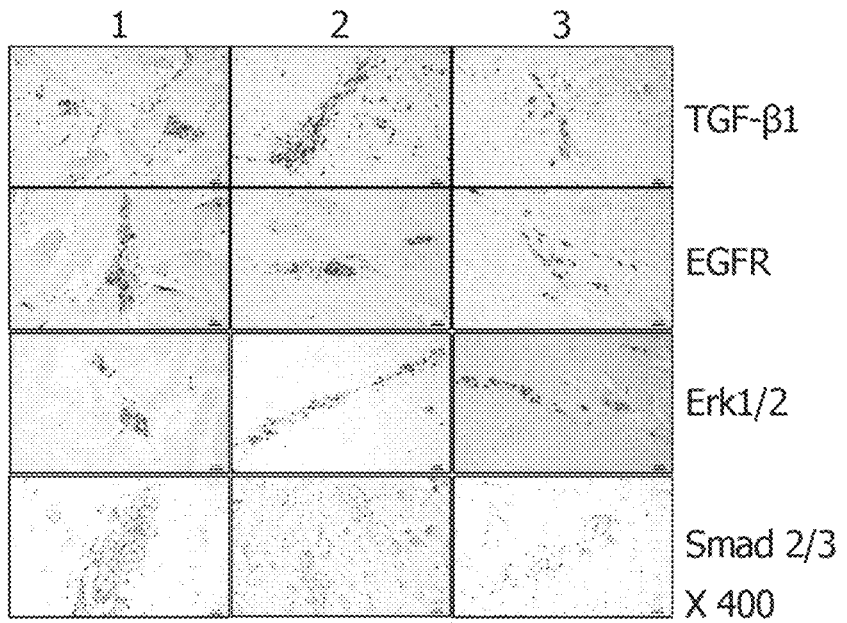
1. Untreated  2. dE1-RGD/GFP/scramble  3. dE1-RGD/GFP/shMot
[FIG. 4E]
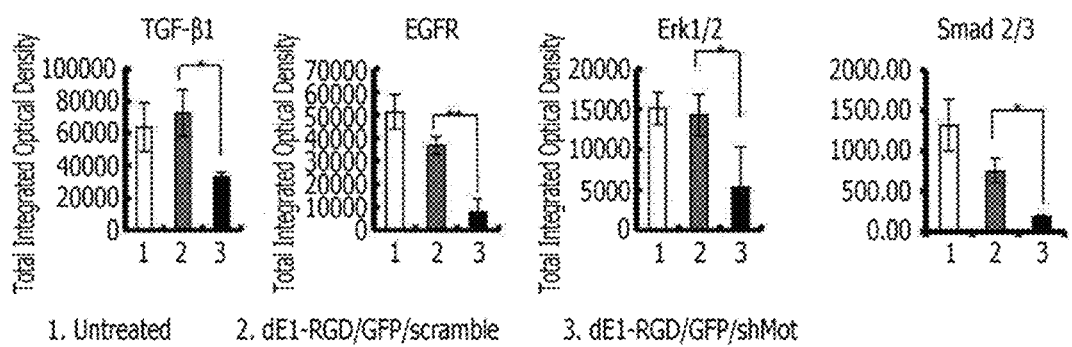
1. Untreated    2. dE1-RGD/GFP/scramble    3. dE1-RGD/GFP/shMot

[FIG. 5A]
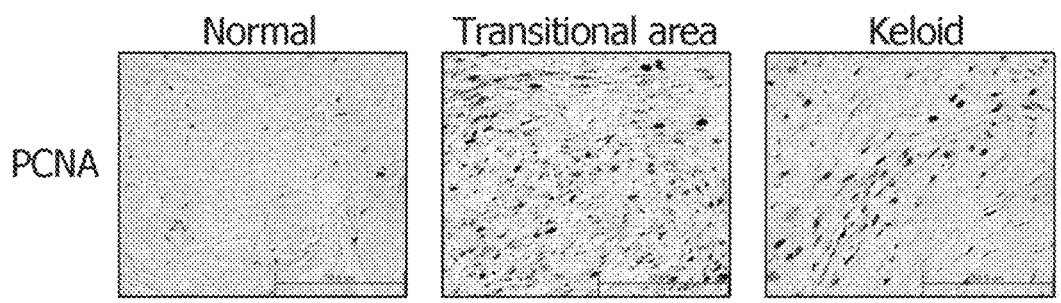
[FIG. 5B]
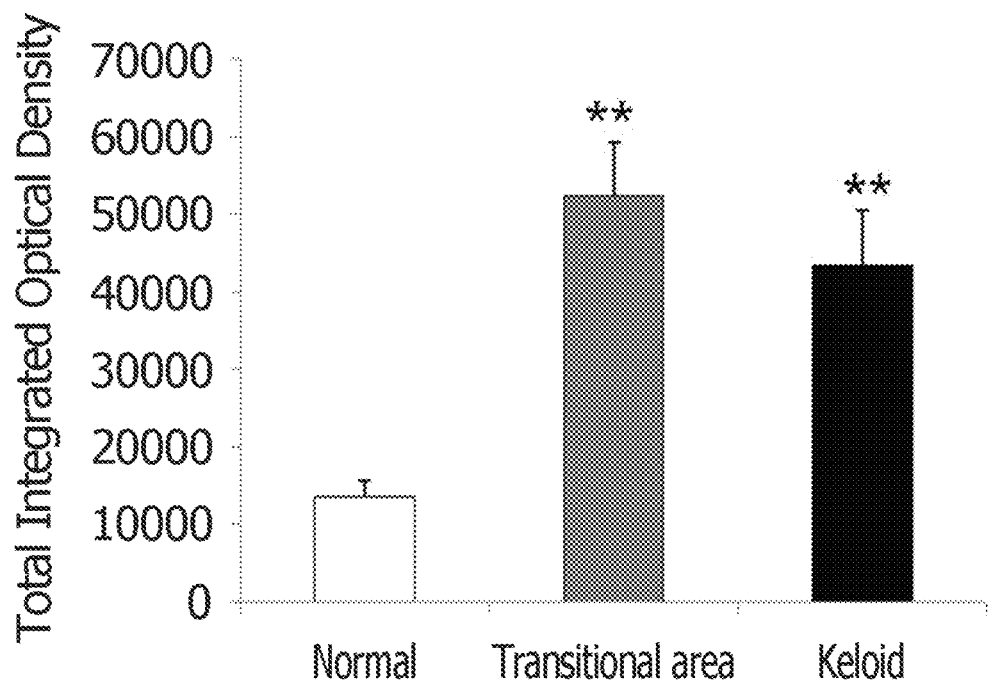

[FIG. 5C]
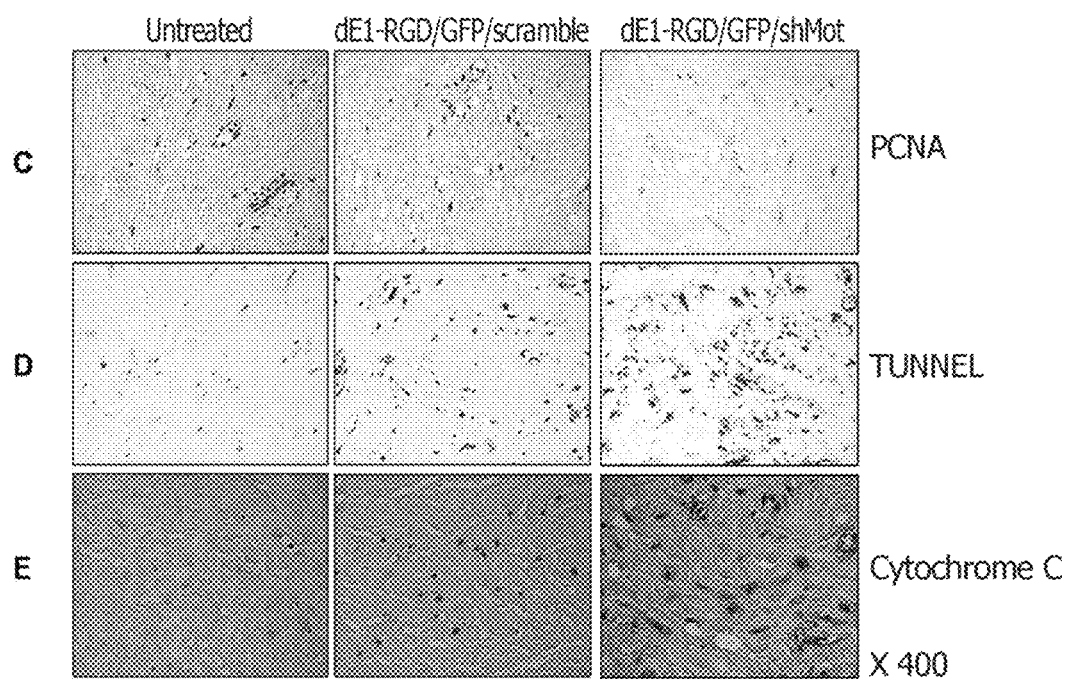
[FIG. 5D]
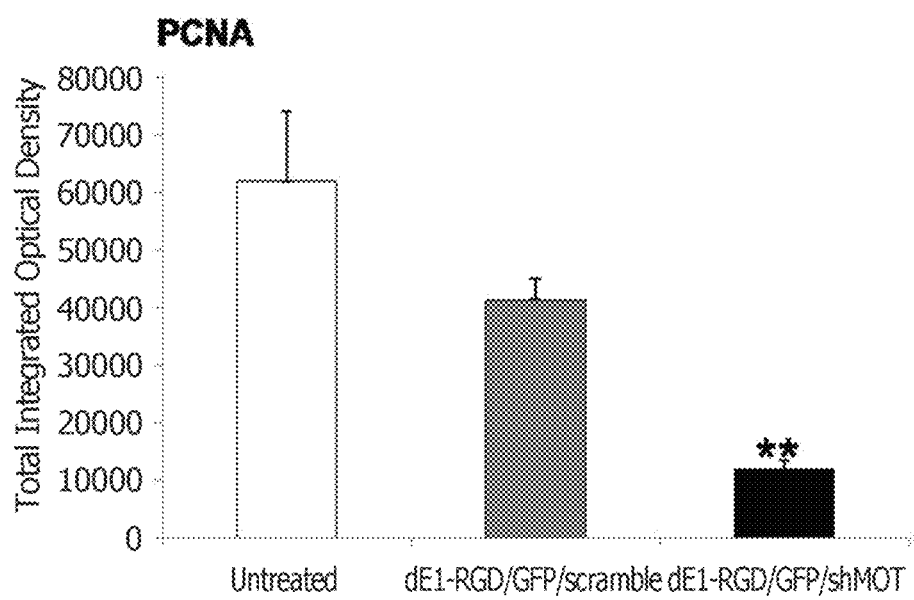

[FIG. 5E]
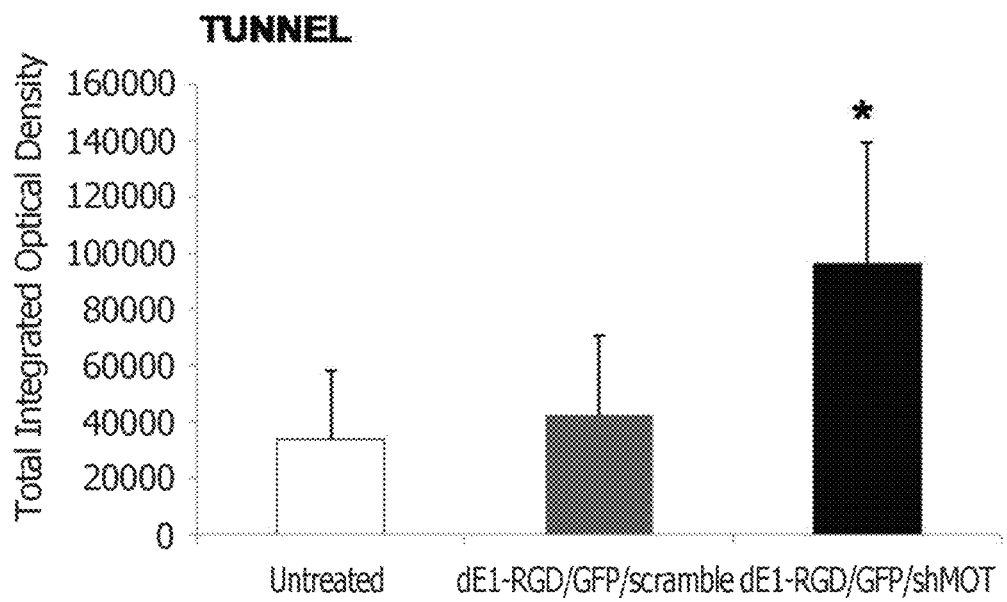
[FIG. 5F]
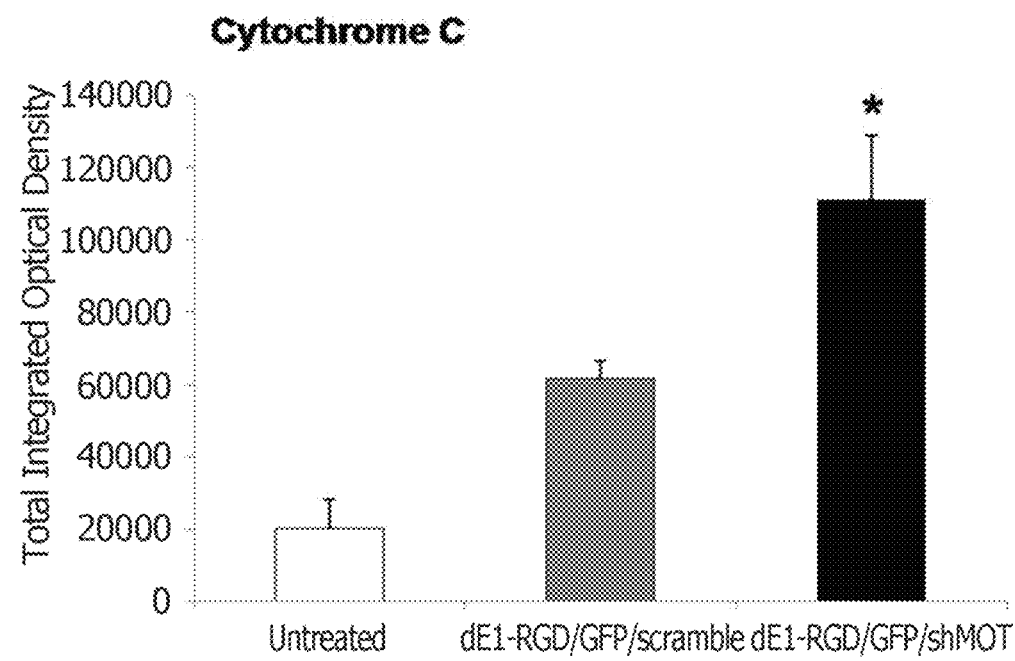

[FIG. 6A]
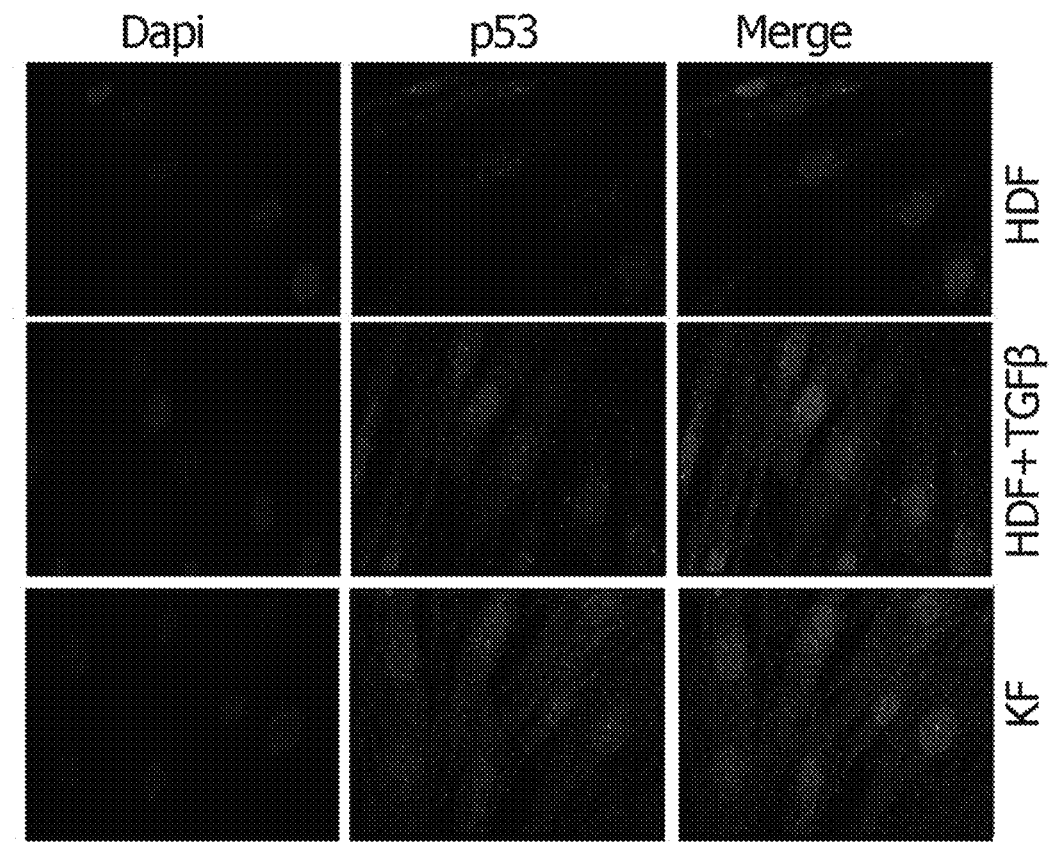
[FIG. 6B]
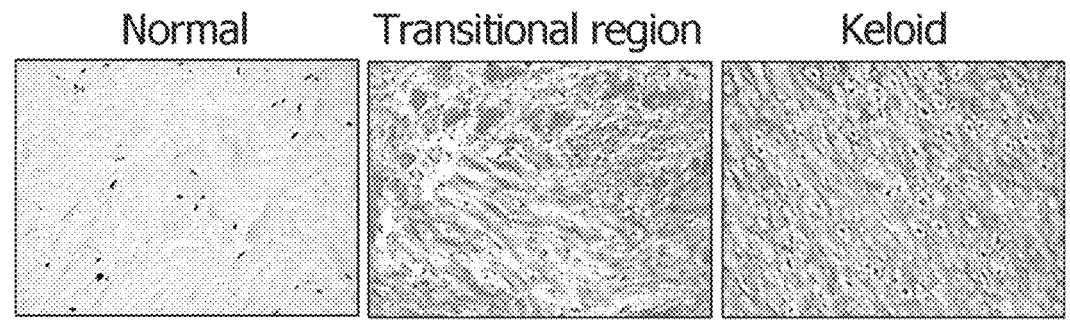

[FIG. 6C]
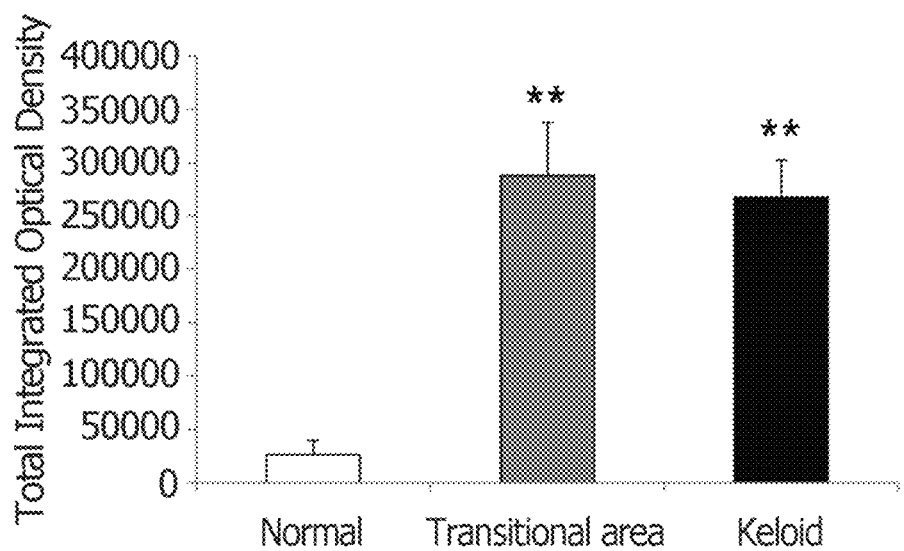
[FIG. 6D]
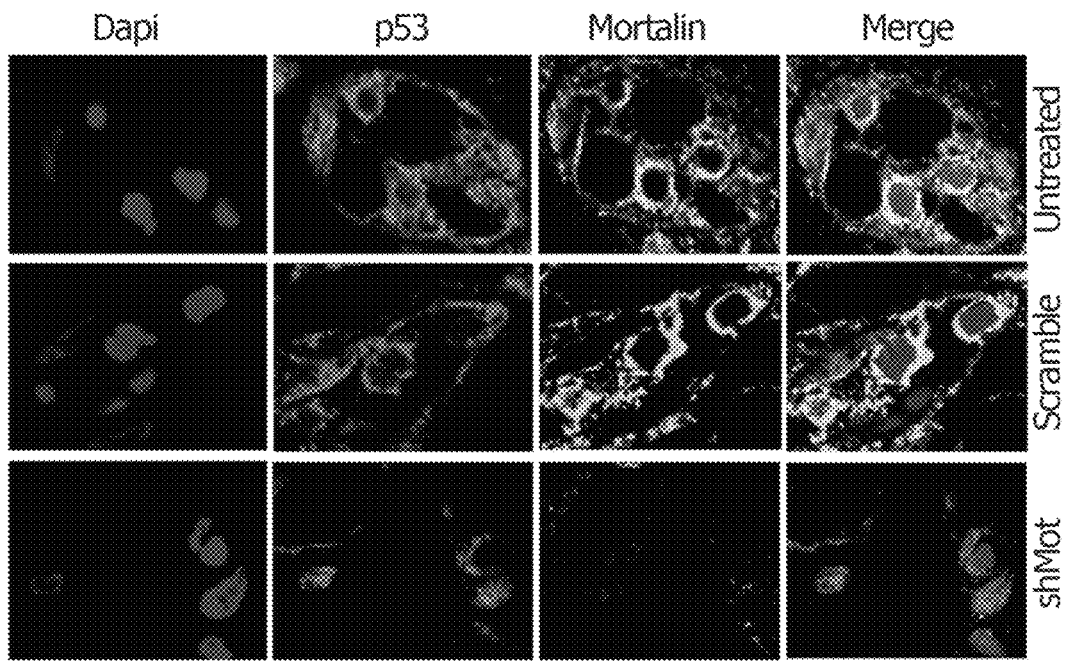

[FIG. 7]
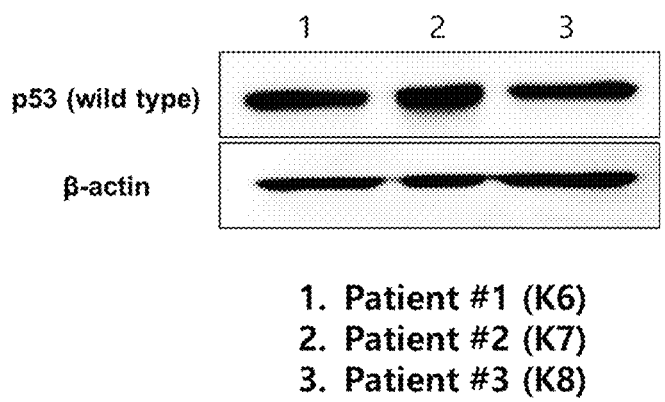
1. Patient #1 (K6)
2. Patient #2 (K7)
3. Patient #3 (K8)
[FIG. 8]
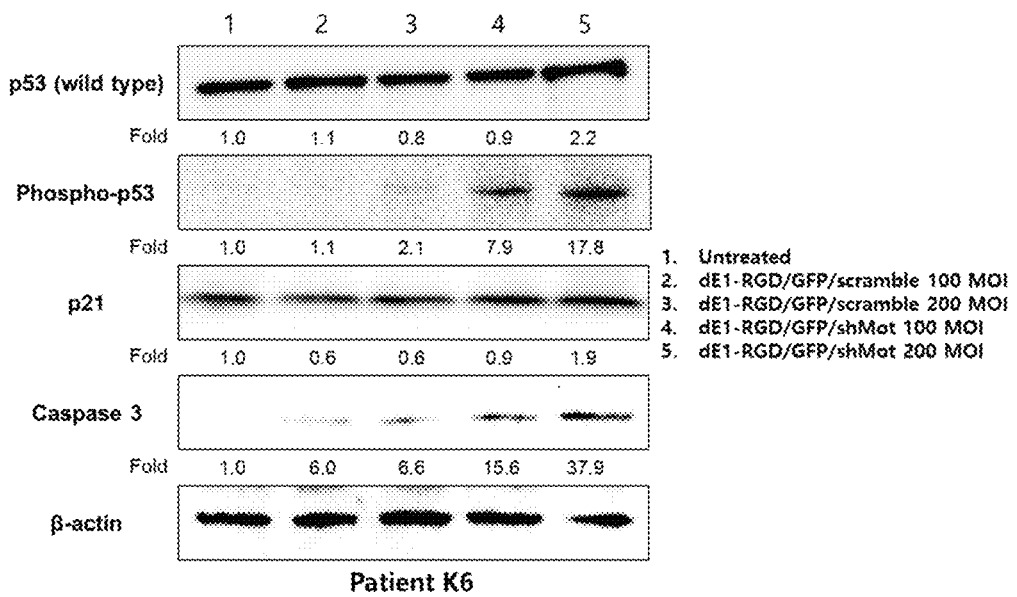

[FIG. 9]
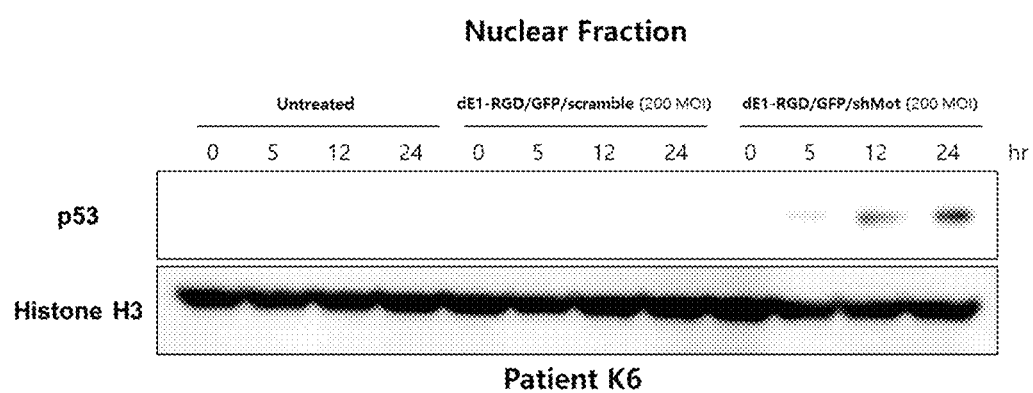

SEQUENCE LISTING

<160> NUMBER OF SEQ ID NOS: 4

<210> SEQ ID NO 1
<211> LENGTH: 64
<212> TYPE: DNA
<213> ORGANISM: Homo sapiens

<400> SEQUENCE: 1
gatcccgcca aaggacaac atatgttcaa gagacatatg ttgtccttct ggcttttttg    60
gaaa                                                                64

<210> SEQ ID NO 2
<211> LENGTH: 2802
<212> TYPE: DNA
<213> ORGANISM: Homo sapiens

<400> SEQUENCE: 2
ggagcgcttg tttgctgcct cgtactcctc catttatccg ccatgataag tgccagccga    60
gctgcagcag cccgtctcgt gggcgccgca gcctcccggg ccctacggc cgcccgccac   120 caggatagct ggaatggcct tagtcatgag gcttttagac ttgtttcaag gcgggattat   180
gcatcagaag caatcaaggg agcagttgtt ggtattgatt tgggtactac caactcctgc   240
gtggcagtta tggaaggtaa acgagcaaag gtgctggaga tgccgaaggt gccagaacc    300 accccttcag ttgtggcctt tacagcagat ggtgagcgac ttgttggaat gccggccaag   360
cgacaggctg tcaccaaccc aaacaataca ttttatgcta ccaagcgtct cattggccgg   420
cgatatgatg atcctgaagt acagaaagac attaaaaatg ttccctttaa aattgtccgt   480
gcctccaatg gtgatgcctg ggttgaggct catgggaaat tgtattctcc gagtcagatt   540
ggagcatttg tgttgatgaa gatgaaagag actgcagaaa attacttggg gcgcacagca   600
aaaaatgctg tgatcacagt cccagcttat ttcaatgact cgcagagaca ggccactaaa   660
gatgctggcc agatatctgg actgaatgtg cttcgggtga ttaatgagcc cacagctgct   720
gctcttgcct atggtctaga caaatcagaa gacaaagtca ttgctgtata tgatttaggt   780
ggtggaactt ttgatatttc tatcctggaa attcagaaag gagtatttga ggtgaaatcc   840
acaaatgggg ataccttctt aggtgggaa gactttgacc aggccttgct acggcacatt   900
gtgaaggagt tcaagagaga gacaggggtt gatttgacta agacaacat ggcacttcag   960 agggtacggg aagctgctga aaaggctaag tgtgaactct cctcatctgt gcagactgac  1020
atcaatttgc cctatcttac aatggattct tctggaccca gcatttgaa tatgaagttg  1080 acccgtgctc aatttgaagg gattgtcact gatctaatca aaggactat cgctccatgc  1140 caaaaagcta tgcaagatgc agaagtcagc aagagtgaca taggagaagt gattcttgtg  1200
ggtggcatga ctaggatgcc caaggttcag cagactgtac aggatctttt tggcagagcc  1260
ccaagtaaag ctgtcaatcc tgatgaggct gtggccattg gagctgccat tcagggaggt  1320
gtgttggccg cgatgtcac ggatgtgctg ctccttgatg tcactcccct gtctctgggt  1380
attgaaactc taggaggtgt ctttaccaaa cttattaata ggaataccac tattccaacc  1440
aagaagagcc aggtattctc tactgccgct gatggtcaaa cgcaagtgga aattaaagtg  1500
tgtcagggtg aaagagagat ggctggagac aacaaactcc ttggacagtt actttgatt  1560 ggaattccac cagcccctcg tggagttcct cagattgaag ttacatttga cattgatgcc  1620
aatgggatag tacatgtttc tgctaaagat aaaggcacag acgtgagca gcagattgta  1680 atccagtctt ctggtggatt aagcaaagat gatattgaaa atatggttaa aaatgcagag  1740

```
aaatatgctg aagaagaccg gcgaaagaag gaacgagttg aagcagttaa tatggctgaa    1800
ggaatcattc acgacacaga aaccaagatg gaagaattca aggaccaatt acctgctgat    1860
gagtgcaaca agctgaaaga agagatttcc aaaatgaggg agctcctggc tagaaaagac    1920
agcgaaacag gagaaaatat tagacaggca gcatcctctc ttcagcaggc atcattgaag    1980
ctgttcgaaa tggcatacaa aaagatggca tctgagcgag aaggctctgg aagttctggc    2040
actggggaac aaaaggaaga tcaaaaggag gaaaaacagt aataatagca gaaattttga    2100
agccagaagg acaacatatg aagcttagga gtgaagagac ttcctgagca gaaatgggcg    2160
aacttcagtc tttttactgt gtttttgcag tattctatat ataatttcct taatttgtaa    2220
atttagtgac cattagctag tgatcattta atggacagtg attctaacag tataaagttc    2280
acaatattct atgtccctag cctgtcattt ttcagctgca tgtaaaagga ggtaggatga    2340
attgatcatt ataaagattt aactatttta tgctgaagtg accatatttt caagggtga    2400 aaccatctcg cacacagcaa tgaaggtagt catccataga cttgaaatga gaccacatat    2460
ggggatgaga tccttctagt tagcctagta ctgctgtact ggcctgtatg tacatggggt    2520
ccttcaactg aggccttgca agtcaagctg gctgtgccat gtttgtagat ggggcagagg    2580
aatctagaac aatgggaaac ttagctattt atattaggta cagctattaa aacaaggtag    2640
gaatgaggct agacctttaa cttccctaag gcatacttt ctagctacct tctgccctgt    2700
gtctggcacc tacatccttg atgattgttc tcttacccat tctggaattt ttttttttt    2760 taaataaata cagaaagcat cttgaaaaaa aaaaaaaaa aa                        2802

<210> SEQ ID NO 3
<211> LENGTH: 64
<212> TYPE: DNA
<213> ORGANISM: Artificial
<220> FEATURE:
<223> OTHER INFORMATION: shRNA - sense

<400> SEQUENCE: 3
gatcccgcca aaggacaac atatgttcaa gagacatatg ttgtccttct ggcttttttg     60
gaaa                                                                 64

<210> SEQ ID NO 4
<211> LENGTH: 64
<212> TYPE: DNA
<213> ORGANISM: Artificial
<220> FEATURE:
<223> OTHER INFORMATION: shRNA - antisense

<400> SEQUENCE: 4
agcttttcca aaaagccag aaggacaaca tatgttcaag acacatatgt tgtccttctg     60
gcgg                                                                 64
```

COMPOSITION FOR PREVENTING OR TREATING KELOID OR HYPERTROPHIC SCARS

CROSS-REFERENCE TO RELATED APPLICATION

This application claims priority to and is a Continuation-In-Part of PCT/KR2017/000154 (WO2017/119744), filed on Jan. 5, 2017 entitled "COMPOSITION FOR PREVENTING OR TREATING KELOID OR HYPERTROPHIC SCARS", which application claims priority to and the benefit of Korean Patent Application No. 10-2016-0001031, filed on Jan. 5, 2016, the disclosures of which are incorporated herein by reference in their entirety. Any disclaimer that may have occurred during the prosecution of the above-referenced applications is hereby expressly rescinded, and reconsideration of all relevant art is respectfully requested.

SEQUENCE STATEMENT

Incorporated by reference herein in its entirety is the Sequence Listing entitled "G18U10C0378P_SEQ_ST25," created Jan. 5, 2017, size of 5 kilobyte.

BACKGROUND

1. Field of the Invention

The present invention relates to a composition for preventing or treating keloids or hypertrophic scars

2. Discussion of Related Art

Mortalin (mtHsp70/PBP74/Grp75) is a heat-non-inducible member of the heat shock protein 70 (Hsp70) family, consists of 679 amino acids (Mw: 73,913 Da), and plays an important role in mitochondrial import, oxidative stress response, regulation of mitochondrial membrane potential, energy generation, intracellular transport, chaperonization, protection against apoptosis, and p53 functionality (15-17). In normal human cells, mortalin is present primarily in the mitochondria, and mediates transcription-independent tumor suppression by inducing mitochondrial permeability and apoptosis (22, 23).

Keloids are defined as benign skin tumors, and develop when the normal tissue repair sequence becomes dysregulated, resulting in a prolonged proliferative and delayed remodeling phase (1-3). This situation appears by the excessive accumulation of the extracellular matrix resulting from the aberrant synthesis and degradation of extracellular matrix proteins. Increased cell proliferation and an imbalance between collagen synthesis and degradation account for the progressive and hypertrophic nature of keloids.

Keloid scars are aggressive, continually grow, and invade the normal skin, and are caused by increased cell proliferation and excess collagen deposition by abnormal fibroblasts. Accordingly, the expression of mortalin associated with the protection against apoptosis in keloids and normal tissues has been studied in the present invention. For experiments on apoptosis and anti-fibrotic effects, mortalin-specific shRNAs (dE1-RGD/GFP/shMOT) were also constructed and injected into keloid spheroids.

Throughout this specification, a number of research papers and patent documents are cited and provided in parentheses. The disclosures of the cited research papers and patent documents are incorporated herein by reference in their entirety to more fully describe the state of the art to which the present invention pertains and the contents of the present invention.

SUMMARY OF THE INVENTION

The present inventors have ardently conducted research to develop a mortalin inhibitor composition for treating keloids and scars. As a result, the present inventors have found that the overexpression of mortalin may cause keloids and scars, and developed a shRNA system capable of inhibiting the expression of mortalin. In particular, the present inventors have confirmed that when tissues of a patient with a keloid disease, in which extracellular matrix proteins are overexpressed, are transfected with adenoviruses expressing shRNA capable of specifically reducing the expression of mortalin to inhibit mortalin expression, expression of collagen type-I/III, elastin, and fibronectin as main components constituting the extracellular matrix is considerably reduced. Thus, the present invention has been completed based on these facts.

Therefore, it is an object of the present invention to provide a pharmaceutical composition for preventing or treating keloid diseases or scars.

It is another object of the present invention to provide a method of screening a substance for preventing or treating keloid diseases or scars.

It is still another object of the present invention to provide a use of an inhibitor, which suppresses an expression of a mortalin gene or an activity of a mortalin protein, for preparing a medicine for preventing or treating keloid diseases or scars.

It is yet another object of the present invention to provide a use of the pharmaceutical composition for preparing a medicine for preventing or treating keloid diseases or scars, wherein the pharmaceutical composition comprises (a) a therapeutically effective amount of an adenovirus expressing an oligonucleotide for inhibiting expression of a mortalin gene as an active ingredient; and (b) a pharmaceutically acceptable carrier.

It is yet another object of the present invention to provide a method of preventing or treating keloid diseases or scars, which comprises administering a therapeutically effective amount of an inhibitor, which suppresses expression of a mortalin gene or an activity of a mortalin protein, to a subject in need thereof.

It is yet another object of the present invention to provide a method of preventing or treating keloid diseases or scars, which comprises administering to a subject in need thereof the pharmaceutical composition, which comprises (a) a therapeutically effective amount of an adenovirus expressing an oligonucleotide for inhibiting expression of a mortalin gene as an active ingredient; and (b) a pharmaceutically acceptable carrier.

Other objects and advantages of the present invention will be more clearly described with reference to the detailed description, claims, and drawings of the present invention.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which:

FIG. 1A, FIG. 1B and FIG. 1C show immunohistochemical staining results of mortalin in human keloid tissues.

(FIG. 1A) Keloid tissues have dense and excessive collagen deposition that extends over the clinical keloid margin into the extra-lesional dermal tissues. (FIG. 1B) The expression of mortalin in keloid tissues (C and D) is higher than that in the adjacent normal tissues (E), especially at the periphery of keloids (D). (FIG. 1C) In the semi-quantitative Metamorph® image analysis, the expression of mortalin was increased 4.8-fold, compared to the adjacent normal tissues. Here, this difference is statistically significant (**p<0.01).

FIG. 2A and FIG. 2B show the results of confirming the expression of a mortalin protein in keloid tissues using Western blots. (FIG. 2A) The expression of the mortalin protein in the keloid tissues is shown to be 25-fold higher than in the normal dermal tissues. (FIG. 2B) The expression of the mortalin protein is shown to be 2.3-fold higher than in the KFs activated by TGF-β 1 (10 ng/mL).

FIG. 3A, FIG. 3B and FIG. 3C show a shMot-expressing adenovirus according to the present invention. (FIG. 3A) shows schematic diagrams of the shMot-expressing adenoviral vectors. The RGD-incorporated adenovirus is generated by inserting a RGD motif between HI-loops of the fiber knob (asterisk). (ITR=inverted terminal repeat; Ψ=packaging signal; pA=poly-A sequence; IX=protein IX; and shMot=mortalin-specific small hairpin (sh)RNAs). (FIG. 3B) shows the mortalin expression in keloid fibroblasts after dE1-RGD/GFP/shMot transduction. Scrambled shRNA which does not target any human gene was used as the control. Overexpressed mortalin in cytosolic and extracellular areas of KFs is knocked down by treatment with dE1-RGD/GFP/shMot. Double immunostaining images of KFs show the mortalin knockdown (mortalin: green, and nucleus: blue; ×200). (FIG. 3C) Similar results are obtained for the primary keloid spheroids infected with dE1-RGD/GFP/shMot (×680).

FIG. 4A, FIG. 4B, FIG. 4C and FIG. 4E show the immunohistochemical staining results of keloid spheroid sections of collagen type I and III, elastin, and fibronectin proteins in dE1-RGD/GFP/shMot-transduced keloid spheroid tissues. (FIG. 4A) shows the Masson's trichrome staining result of keloid spheroids. After the treatment with dE1-RGD/GFP/shMot, dense and coarse collagen bundles are converted into thin and shallow collagen bundles. Original magnification: ×400. (FIG. 4B) shows that the expression of the ECM components including collagen type I and III, elastin, and fibronectin proteins is reduced in the keloid spheroids transduced with dE1-RGD/GFP/shMot, compared to the keloid spheroids transduced with a scramble virus. Original magnification: ×400. (FIG. 4C) shows the results of semi-quantitative image analysis for expression of collagen type I and III, elastin and fibronectin proteins. The expression of the proteins in the keloid spheroids transduced with dE1-RGD/GFP/shMot is remarkably reduced, compared to the scramble virus-transduced keloids (**p<0.01). (FIG. 4D) The expression of TGF-β1, EGFR, Smad 2/3 complex and Erk 1/2 proteins in the primary keloid spheroids is reduced by the mortalin-specific shRNA-expressing adenovirus (×400). (FIG. 4E) The expression levels of TGF-β1, EGFR, Smad 2/3 complex and Erk 1/2 proteins in the mortalin-specific shRNA-expressing adenovirus-treated keloid spheroids are reduced by 52%, 43%, 11%, and 42%, respectively, compared to the scramble virus-transduced spheroids (*p<0.05, **p<0.01).

FIG. 5A, FIG. 5B, FIG. 5C, FIG. 5D, FIG. 5E and FIG. 5F show that mortalin knockdown reduces PCNA expression and induces apoptosis. (FIG. 5A) shows the immunohistochemical staining results of PCNA in keloid tissues (n=3). It can be seen that the cell division actively occurs in the keloid tissues, compared to the normal tissues. (FIG. 5B) The expression levels of PCNA proteins in central and transitional keloids are remarkably increased 3.9-fold and 3.2-fold, respectively, compared to the adjacent normal tissues (**p<0.01). (FIG. 5C to FIG. 5F) Reduced PCNA expression and increased apoptosis as observed by TUNEL staining of the dE1-RGD/GFP/shMot-treated spheroids. The expression of a cytochrome-C protein increases 1.8-fold after transduction with dE1-RGD/GFP/shMot (*p<0.05; **p<0.01). Original magnification: ×400.

FIG. 6A, FIG. 6B, FIG. 6C and FIG. 6D show that mortalin interacts with p53 and mortalin knockdown relocates p53 into the cell nucleus in primary keloid spheroids. (FIG. 6A) shows the results of p53 immunofluorescence staining of HDFs, TGF-β1-activated HDFs, and KFs. A clear localization of p53 is observed in the cytoplasm and nuclei of TGF-β1-activated HDFs and KFs, compared to HDFs (p53: red, and nucleus: blue; ×680). (FIG. 6B and FIG. 6C) Expression of a p53 protein in the central and transitional keloids markedly increases approximately 10-fold, compared to the adjacent normal tissues (n=6) (**p<0.01). (FIG. 6D) Mortalin silencing-induced apoptosis is mediated by nuclear translocation of mutant p53. Colocalization of p53 and mortalin in the cytosol is observed in the untreated keloid spheroids. Double immunostaining images of mortalin-specific shRNA-expressing adenovirus-treated keloid spheroids show the mortalin knockdown-induced nuclear translocation of p53 (mortalin: green, p53: red, and DAPI: blue).

FIG. 7 shows a result of immunoblotting analysis that was performed to analyze the expression levels of wild type p53 in several primary keloid fibroblasts of Patients #1 (Case No. K6); Patients #2 (Case No. K7); and Patients #3 (Case No. K8).

FIG. 8 shows a result of immunoblotting analysis that was performed to analyze the expression levels of wild type p53, phospho-p53, p21, and caspase 3 in primary keloid fibroblast after transduction with either dE1-RGD/GFP/scramble or dE1-RGD/GFP/shMot (100 and 200 MOI) (patient Case No. K6).

FIG. 9 shows a result of nuclear p53 expression level in primary keloid fibroblast that was analyzed by western blotting at multiple time points following transduction with either dE1-RGD/GFP/scramble or dE1-RGD/GFP/shMot (200 MOI).

DETAILED DESCRIPTION OF EXEMPLARY EMBODIMENTS

According to one aspect of the present invention, the present invention relates th a pharmaceutical composition for preventing or treating keloid diseases or scars, which comprises, as an active ingredient, an inhibitor that suppresses expression of a mortalin gene or suppresses an activity of a mortalin protein.

According to another aspect of the present invention, there is provided a pharmaceutical composition for preventing or treating keloid diseases or scars, which comprises an oligonucleotide for inhibiting the expression of the mortalin gene as an active ingredient.

The present inventors have ardently conducted research to develop a mortalin inhibitor composition for treating keloids and scars. As a result, the present inventors have found that the overexpression of mortalin may cause keloids and scars, and developed a shRNA system capable of inhibiting the expression of mortalin. In particular, the present inventors have confirmed that when tissues of a patient with a keloid disease, in which extracellular matrix proteins are overexpressed, are transfected with adenoviruses expressing shRNA capable of specifically reducing the expression of mortalin to inhibit mortalin expression, expression of collagen type-I/III, elastin, and fibronectin as main components constituting the extracellular matrix is considerably reduced.

The present inventors have confirmed mortalin expressions in keloids and normal tissues using Western blotting and immunohistochemical staining. After dE1-RGD/GFP/shMOT was transduced into primary keloid spheroids, expression levels of main extracellular matrix (ECM) proteins (EGFR, TGF-β 1, Erk 1/2, and a Smad 2/3 complex) were measured immunohistochemically. Also, an immunofluorescence assay was performed to confirm the interaction between mortalin and p53. The expression of mortalin was increased in keloid tissues, compared to the neighboring normal tissues and activated KFs. When mortalin was knocked down in the primary keloid spheroids, the expressions of collagen type I and III, fibronectin and elastin were remarkably reduced, and the expressions of TGF-β 1, EGFR, Erk 1/2, and Smad 2/3 complex proteins were also reduced. Also, decreased TUNEL activity and decreased cytochrome-C were observed, and the knockdown of mortalin relocated p53 to the cell nucleus in the dE1-RGD/GFP/shMOT-transfected primary keloid spheroids. These results support that the knockdown of mortalin induces apoptosis and reduces ECM expression in a keloid spheroid, which may be highly useful for treating keloids.

The composition of the present invention is for preventing and/or treating keloid and hypertrophic scars. For example, the composition of the present invention may be used to alleviate, prevent or treat postoperative scars, burn keloids, keloids, posttraumatic keloids, restenosis after percutaneous coronary angioplasty, hypertrophic scar pannus, and the like. Meanwhile, scars may also be prevented when the composition of the present invention is administered during surgery.

In this specification, the term "treatment" refers to (i) prevention of keloids or scars; (ii) inhibition of formation or improvement of keloids or scars; and (iii) alleviation of disorders or diseases associated with the inhibition of formation or improvement of keloids or scars. Therefore, in this specification, the term "therapeutically effective amount" refers to an amount sufficient to achieve the pharmacological effect.

In the present invention, a sequence of a mortalin gene is GeneBank Accession No: BC000478.2 (SEQ ID NO: 2).

According to one exemplary embodiment of the present invention, the composition of the present invention may comprise an inhibitor, which suppresses expression of a mortalin gene or suppresses the activity of a mortalin protein, as an active ingredient. Here, the active ingredient may comprise short hairpin RNA (shRNA), small interfering RNA (siRNA), microRNA (miRNA), a ribozyme, a DNAzyme, a peptide nucleic acid (PNA), an antisense oligonucleotide, an antibody, an aptamer, a natural extract, or a chemical. According to another exemplary embodiment of the present invention, the oligonucleotide is shRNA, siRNA, miRNA, or an antisense oligonucleotide. In the present invention, the oligonucleotide comprises a sequence complementary to a sequence from 2,102th nucleotide to 2,120th nucleotide of SEQ ID NO: 2.

According to specific exemplary embodiments of the present invention, the pharmaceutical composition of the present invention comprises shRNA having a sequence complementary to a nucleotide sequence of SEQ ID NO: 1.

The term "shRNA" or "short hairpin RNA" used in this specification refers to single-stranded RNA having a length of 45 to 70 nucleotides. Here, oligo DNA connecting a 3-10 base linker between a sense strand of a siRNA base sequence of a target gene and a nonsense strand complementary to the sense strand is synthesized, and then cloned into a plasmid vector, or inserted into a retrovirus such as a lentivirus and an adenovirus. By the expressing the vector or the retrovirus shRNA having a looped hairpin structure is formed, and then converted into siRNA by intracellular Dicer to show RNAi effects. According to specific exemplary embodiments of the present invention, the shRNA of the present invention inhibiting the expression of the mortalin gene comprises sequences of SEQ ID NOS: 3 and SEQ ID NOS: 4. The sequence of SEQ ID NO: 3 is a sequence of sense strand, and the sequence of SEQ ID NO: 4 is an sequence of antisense strand.

In the present invention, the term "siRNA" refers to a nucleic acid molecule that may mediate RNA interference or gene silencing (see WO 00/44895, WO 01/36646, WO 99/32619, WO 01/29058, WO 99/07409, and WO 00/44914). Because the siRNA may inhibit the expression of a target gene, the siRNA is provided for an effective gene knockdown method or a gene therapy. siRNA was first found in plants, insects, *Drosophila*, and parasites, but a variety of siRNAs have recently been developed and used to be applied to mammalian cell research (Degot S, et al. 2002; Degot S, et al. 2004; Ballut L, et al. 2005).

A siRNA molecule of the present invention may have a structure in which a sense strand (a sequence corresponding to a mortalin mRNA sequence) and an antisense strand (a sequence complementary to the mortalin mRNA sequence) are located opposite each other to form a double stranded structure. Alternatively, the siRNA molecule of the present invention may have a single-stranded structure having a self-complementary sense strand and an antisense strand. The siRNA may comprise, but is not limited to, a complete pair of a double-stranded RNA region forming RNA pairs, as well as unpaired regions formed by a mismatch (the corresponding bases are not complementary to each other), a bulge (there are no corresponding bases in a one-way strand), and the like. The overall length of siRNA is in a range of 10 to 100 bases, preferably 15 to 80 bases, more preferably 20 to 70 bases, and most preferably 20-30 bases.

The term, "microRNA" or "miRNA" used in this specification refers to a single-stranded RNA molecule having a length of 21 to 25 nucleotides, which is a regulatory substance that controls gene expression in eukaryotes via the suppression of target mRNA in a disruption or translation phase. Such miRNA is formed by two-step processing. An initial miRNA transcript (primary miRNA) is cleaved in the nuclei by an RNaseIII type enzyme referred to as Drosha, resulting in a stem-loop structure consisting of 70 to 90 bases, that is, premiRNA. Then, the premiRNA is translocated into the cytoplasm, and cleaved by an enzyme referred to as Dicer to form mature miRNA consisting of 21 to 25 bases. The miRNA thus formed complementarily binds to the target mRNA to serve as a post-transcriptional gene suppressor and induce translational inhibition and mRNA destabilization. The miRNA is involved in various physiological phenomena and diseases.

The term "antisense oligonucleotide" used in this specification refers to DNA or RNA, or a derivative thereof, which contains a nucleic acid sequence complementary to certain mRNA, and serves to bind to a complementary sequence in the mRNA in order to inhibit the translation of mRNA into a protein. The antisense sequence of the present invention refers to a DNA or RNA sequence that is complementary to the mortalin gene, may bind to mRNA of the mortalin gene, and may inhibit essential activities of translation of mortalin mRNA, translocation into the cytoplasm, maturation, or other overall biological functions. An antisense nucleic acid has a length of 6 to 100 bases, preferably 8 to 60 bases, and more preferably 10 to 40 bases.

In the pharmaceutical composition of the present invention, the shRNA, siRNA, miRNA or antisense oligonucleotide suppresses the interaction between mortalin and p53 in the cytoplasm by inhibiting mortalin expression. As a result, p53 is translocated into the cell nucleus to cause effects such as apoptosis, and the like.

According to another aspect of the present invention, the present invention provides a pharmaceutical composition for preventing or treating keloid diseases or scars, which comprises (a) a therapeutically effective amount of an adenovirus expressing an oligonucleotide for inhibiting expression of a mortalin gene as an active ingredient; and (b) a pharmaceutically acceptable carrier.

Because the recombinant adenovirus included in the composition of the present invention exhibits an apoptotic effect on keloid tissues, the pharmaceutical composition of the present invention may be used to alleviate, prevent or treat various diseases leaving keloids or scars, for example postoperative scars, burn keloids, keloids, posttraumatic keloids, restenosis after percutaneous coronary angioplasty, hypertrophic scar pannus, and the like.

According to one exemplary embodiment of the present invention, the adenovirus comprises the following sequences:

(a) an inverted terminal repeat (ITR) sequence of the adenovirus;

(b) an oligonucleotide sequence for inhibiting the expression of a mortalin gene, which comprises a sequence complementary to a sequence from 2,102th nucleotide to 2,120th nucleotide of SEQ ID NO: 2; and (c) a promoter sequence located downstream of the oligonucleotide sequence.

In the composition, the oligonucleotide for inhibiting the expression of the mortalin gene is shRNA, siRNA, miRNA, or an antisense oligonucleotide.

An adenovirus has been widely used as a gene transfer vector because the adenovirus has a medium genome size, is easily manipulated, and exhibits a high titer, a wide spectrum of target cells, and excellent infection potential. Both termini of the genome comprise a 100 to 200 bp-long inverted terminal repeat (ITR), which is a cis-element essential for DNA replication and packaging. E1 regions (E1A and E1B) of the genome encode proteins that regulate the transcription of transcriptional and host cell genes. The E2 regions (E2A and E2B) encode proteins that are involved in viral DNA replication.

Among the currently developed adenovirus vectors, a replication-deficient adenovirus lacking the E1 region has been widely used. Meanwhile, the E3 region is removed from a conventional adenovirus vector to provide a site into which a foreign gene is inserted (Thimmappaya, B. et al., Cell, 31:543-551(1982); and Riordan, J. R. et al., Science, 245:1066-1073(1989)). Thus, the oligonucleotide sequence of the present invention for inhibiting mortalin expression is preferably inserted into the deleted E1 region (E1A region and/or E1B region, preferably E1B region) or E3 region, and more preferably inserted into the deleted E3 region. Meanwhile, a target nucleotide sequence to be delivered into the cells is preferably inserted into the deleted E1 region (E1A region and/or E1B region, preferably E1B region) or E3 region, and more preferably inserted into the deleted E1 region. Also, the insert sequences may also be inserted into a deleted E4 region. In this specification, the term "deletion" used in connection with a viral genome sequence has a meaning encompassing complete deletion of the corresponding sequence, as well as partial deletion or substitution of the sequence.

According to the most preferred embodiment of the present invention, an adenoviral gene delivery system of the present invention has a structure in which a "promoter-detectable tag-expressing nucleotide sequence-polyA sequence" and a "promoter-targeting nucleotide sequence gene-polyA sequence" are linked to each other. The promoter-detectable tag-expressing nucleotide sequence-polyA sequence is inserted into the deleted E1 region (E1A region and/or E1B region, preferably E1B region) or E3 region, preferably inserted into the deleted E1 region, and the "promoter-targeting nucleotide sequence gene-polyA sequence" is inserted into the deleted E1 region (E1A region and/or E1B region, preferably E1B region) or E3 region, preferably inserted into the deleted E3 region. Also, the insert sequences may be inserted into a deleted E4 region.

According to one exemplary embodiment of the present invention, the adenovirus of the present invention further comprises an RGD motif sequence (asterisk) in upstream of the mortalin-inhibiting oligonucleotide sequence (shMot) (see FIG. 3A). More specifically, the adenovirus of the present invention is an RGD-incorporated adenovirus obtained by inserting an RGD (ArgGlyAsp) motif between HI-loops of a fiber knob (asterisk).

The pharmaceutically acceptable carrier included in the composition of the present invention is typically used in preparations, and comprises lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate and mineral oil, but the present invention is not limited thereto. In addition to the aforementioned components, the pharmaceutical composition of the present invention may further include a lubricant, a wetting agent, a sweetening agent, a flavoring agent, an emulsifying agent, a suspending agent, a preservative, and the like.

The pharmaceutical composition of the present invention is preferably parenterally administered. For example, the pharmaceutical composition may be administered by intravenous, intraperitoneal, intratumoral, intramuscular, subcutaneous, hepatoportal, hepatoarterial, or local administration.

An appropriate dose of the pharmaceutical composition of the present invention may vary depending on factors as a preparation method, an administration mode, the age, weight and sex of a patient, the severity of symptoms of a disease, a diet, a duration of administration, a route of administration, a secretion rate, and the sensitivity to response. Generally, a skilled physician may easily determine and prescribe the dose of the composition effective for desired treatment. In general, the pharmaceutical composition of the present invention comprises $1\times10^5$ to $1\times10^{15}$ PFU/mL of a recombinant adenovirus, and is typically injected at a dose of $1\times10^{10}$ PFU once per 2 days over 2 weeks.

The pharmaceutical composition of the present invention may be formulated using a pharmaceutically acceptable carrier and/or excipient, according to methods which may be easily carried out by a person having ordinary skill in the art to which the present invention belongs, so that the pharmaceutical composition is prepared in a unit dosage form, or may be prepared by introduction into a high-dose container. In this case, a formulation may be in the form of a solution, a suspension or an emulsion in an oily or aqueous medium, or in the form of an extract, a powder, a granule, a tablet or a capsule, and may further include a dispersing agent or a stabilizing agent.

According to still another aspect of the present invention, the present invention provides a method of screening a substance for preventing or treating keloid diseases or scars, which comprises:

(a) treating keloid tissues or keloid cells with a test substance; and (b) analyzing an expression level of an intracellular mortalin gene in the tissues or cells treated with the test substance, wherein the test substance is judged to be the substance for preventing or treating keloid diseases or scars when the expression of the intracellular mortalin gene is reduced or the expression of a mortalin protein is reduced.

According to the method of the present invention, first of all, a test substance to be analyzed is allowed to come into contact with keloid tissues or keloid cells. Preferably, the keloid tissues or keloid cells are human keloid tissues or keloid fibroblasts. The term "test substance(s)" used with reference to the screening method of the present invention refers to an unknown substance that is used for screening in order to examine whether it has an effect on an expression level of a mortalin gene or an amount or activity of a mortalin protein. The test substance comprises chemicals, nucleotides, antisense-RNA, shRNA, miRNA, small interfering RNA (siRNA), and natural product extracts, but the present invention is not limited thereto.

Accordingly, an expression level of the intracellular mortalin gene in the tissues or cells treated with the test substance is determined. The results of measurement show that the test substance may be judged to be a substance for preventing or treating keloid diseases or scars when the expression of the intracellular mortalin gene is reduced or the expression of the mortalin protein is reduced.

A change in expression level of the mortalin gene may be measured using various methods known in the related art. For example, the measurement may be performed using RT-PCR (Sambrook et al., *Molecular Cloning. A Laboratory Manual*, 3rd ed. Cold Spring Harbor Press (2001)), Northern blotting (Peter B. Kaufma et al., *Molecular and Cellular Methods in Biology and Medicine*, 102-108, CRC press), hybridization using a cDNA microarray (Sambrook et al., *Molecular Cloning. A Laboratory Manual*, 3rd ed. Cold Spring Harbor Press (2001)), Western blotting or in situ hybridization (Sambrook et al., *Molecular Cloning. A Laboratory Manual*, 3rd ed. Cold Spring Harbor Press (2001)).

According to yet another aspect of the present invention, the present invention provides a method of screening a substance for preventing or treating keloid diseases or scars, which comprises:

(a) treating keloid tissues or keloid cells with a test substance; and (b) analyzing an expression level of an intracellular mortalin or p53 gene or an interaction between the mortalin and p53 in the tissues or cells treated with the test substance, wherein the test substance is judged to be the substance for preventing or treating keloid diseases or scars when the expression of mortalin or p53 in the cytoplasm is reduced or the interaction between mortalin and p53 in the cytoplasm is reduced.

According to the method of the present invention, first of all, a test substance to be analyzed is allowed to come into contact with keloid tissues or keloid cells. Preferably, the keloid tissues or keloid cells are human keloid tissues or keloid fibroblasts. The term "test substance(s)" used with reference to the screening method of the present invention refers to an unknown substance that is used for screening in order to examine whether it has an effect on an expression level of a mortalin or p53 gene or an amount or activity of a mortalin or p53 protein or an interaction between mortalin and p53. The test substance comprises chemicals, nucleotides, antisense-RNA, shRNA, miRNA, small interfering RNA (siRNA), and natural product extracts, but the present invention is not limited thereto.

Next, an expression level of the intracellular mortalin or p53 gene and an interaction between the mortalin and p53 in the tissues or cells treated with the test substance is analyzed. The results of measurement show that the test substance may be judged to be the substance for preventing or treating keloid diseases or scars when the expression of mortalin or p53 in the cytoplasm is reduced or the interaction between mortalin and p53 in the cytoplasm is reduced.

A change in expression level of the mortalin or p53 gene may be measured using various methods known in the related art. For example, the measurement may be performed using RT-PCR (Sambrook et al., *Molecular Cloning. A Laboratory Manual*, 3rd ed. Cold Spring Harbor Press (2001)), Northern blotting (Peter B. Kaufma et al., *Molecular and Cellular Methods in Biology and Medicine*, 102-108, CRC press), hybridization using a cDNA microarray (Sambrook et al., *Molecular Cloning. A Laboratory Manual*, 3rd ed. Cold Spring Harbor Press (2001)), Western blotting or in situ hybridization (Sambrook et al., *Molecular Cloning. A Laboratory Manual*, 3rd ed. Cold Spring Harbor Press (2001)).

The interaction between the mortalin and p53 proteins may be analyzed using various immunoassay methods known in the related art. For example, the interaction between the mortalin and p53 proteins is determined using methods including a radioimmunoassay, radioimmunoprecipitation, immunoprecipitation, an enzyme-linked immunosorbent assay (ELISA), capture-ELISA, an inhibition or competitive assay, and a sandwich assay, but the present invention is not limited thereto. The immunoassay or immunostaining method is disclosed in *Enzyme Immunoassay*, E. T. Maggio, ed., CRC Press, Boca Raton, Fla., 1980; Gaastra, W., *Enzyme-linked immunosorbent assay (ELISA), in Methods in Molecular Biology*, Vol. 1, Walker, J. M. ed., Humana Press, N J, 1984; and Ed Harlow and David Lane, *Using Antibodies: A Laboratory Manual*, Cold Spring Harbor Laboratory Press, 1999, the disclosures of which are incorporated herein by reference in their entirety.

The characteristics and advantages of the present invention are summarized, as follows:

(a) The present invention relates to a pharmaceutical composition for preventing or treating keloid diseases or scars.

(b) The present inventors propose that the inhibition of expression of mortalin and the interaction between mortalin and p53 can be new targets for keloid treatment.

(c) In the present invention, a mortalin-specific shRNA (dE1-RGD/GFP/shMOT) is constructed and injected into keloid spheroids to check an apoptotic and anti-fibrotic effect.

(d) Thus, mortalin knockdown can be effectively used for keloid treatment because the mortalin knockdown induces apoptosis in the keloid spheroids and reduces ECM expression.

Hereinafter, the present invention will be described in detail with reference to embodiments thereof. However, it will be apparent to those skilled in the art that that the description proposed herein is just a preferable example for the purpose of illustration only, not intended to limit the scope of the invention.

EXAMPLES

Experimental Reagents and Methods

Human Dermal Fibroblast, Keloid Tissue and Keloid-Derived Fibroblast

Human normal dermal fibroblasts (HDFs) and keloid fibroblasts (KFs) were obtained from the American Type Culture Collection (ATCC, Manassas, Va.). Keloid tissues and normal abdominal dermal tissues were obtained with approval by the Institutional Review Board of the College of Medicine of Yonsei University. The keloid fibroblasts were obtained from the central dermal layer of keloids. All experiments were performed according to the Helsinki guidelines. Cells were cultured in a Dulbecco's Modified Eagle's medium (DMEM; GIBCO, Grand Island, N.Y.) supplemented with 10% fetal bovine serum (FBS), penicillin (100 U/mL), and streptomycin (100 µg/mL). Demographic information and description of keloids obtained from study subjects are shown in Table 1.

TABLE 1

| Case (no.) | Sex | Age (years) | Keloid site | Used for |
|---|---|---|---|---|
| K1 | M | 31 | Chest | IHC |
| K2 | F | 33 | Ear lobe | IHC |
| K3 | F | 11 | Knee | IHC, spheroid |
| K4 | F | 50 | Anterior chest | IHC |
| K5 | F | 5 | Ankle | IHC |
| K6 | F | 18 | Earlobe | WB |
| K7 | F | 17 | Earlobe | WB, spheroid, IHC |
| K8 | M | 53 | Shoulder | WB, spheroid Immunofluorescence |
| K9 | F | 18 | Earlobe | Immunofluorescence |
| K10 | F | 26 | Earlobe | Immunofluorescence |
| K11 | F | 24 | Earlobe | Immunofluorescence Spheroid, IHC |
| K12 | F | 33 | Abdomen | Immunofluorescence Spheroid, IHC |
| K13 | M | 4 | Neck | Spheroid, IHC |

Immunohistochemical (IHC) Experiments of Mortalin, p53, and PCNA

A formaldehyde-fixed tissue was transferred to a paraffin block, and microtomed into slices with a thickness of 4 µm. After paraffin and moisture were removed from the tissue, the tissue was treated with methanol containing 1% hydrogen peroxide at room temperature for 10 minutes to suppress endogenous peroxidase activity. The tissue sections were treated with a mouse anti-mortalin monoclonal antibody (C1-3), a rabbit anti-p53 (sc-6243 Santa Cruz Biotechnology, Santa Cruz, Calif.) primary antibody, and a mouse anti-PCNA (M0879 DAKO, Carpinteria, Calif.) primary antibody, and reacted overnight at 4° C. After the tissue sections were reacted with a secondary antibody (Super Sensitive™ Polymer-HRP IHC, BioGenex) at room temperature for an hour, the tissue sections were treated with 0.05% diaminobenzidine and 0.003% hydrogen peroxide, and the bound complexes were observed. The sections were stained with Harris hematoxylin, dehydrated, and mounted. Levels of mortalin, p53, and PCNA proteins were analyzed in a semi-quantitative manner using MetaMorph® image analysis software (Universal Image Corp., Buckingham-shire, UK). The results were expressed as the mean optical density for six different digital images per sample.

Construction of shMot-Expressing Adenovirus Vector

A shMot (dE1-RGD/GFP/shMot; Ad-shMot)-expressing, replication-incompetent Ad and the control Ad (dE1-RGD/GFP/scramble; Ad-scramble) were used (FIG. 3). To generate Ads expressing GFP and shMot or scramble in the E1 and E3 regions, respectively, pdE1-RGD/GFP[29] was linearized by SpeI digestion, and *Escherichia coli* BJ5183 was co-transformed with the linearized pdE1-RGD/GFP together with an XmnI-digested pSP72-E3/CMV-shMot or -scramble E3 shuttle vector[30]. The growth, purification and Ad titration were performed according to the prior art[31,32].

Preparation and Adenoviral Transduction of Keloid Spheroids

Keloid tissues were obtained from active-stage keloid patients (n=5). Keloid spheroids were prepared by dissecting keloid central dermal tissues into 2-mm diameter pieces using sterile 21-gauge needles. Explants were planted onto a HydroCell 24 multi-well plate (Nunc, Rochester, N.Y.), and cultured for 4 hours in Isocove's modified Dulbecco's medium (IMDM, Gibco BRL) supplemented with 5% FBS (fetal bovine serum), 10 mM $l^{-1}$ insulin, and 1 mM $l^{-1}$ hydrocortisone. Each of the Ads (dE1-RGD/GFP/shMot and dE1-RGD/GFP/scramble) at $1 \times 10^{10}$ VP was added into plates containing keloid spheroids, and incubated at 37° C. in a 5% $CO_2$ incubator for 3 days. The transduced keloid spheroids were then fixed with 10% formalin, embedded into paraffin, and cut into 5-µm-thick sections.

Histology and Immunohistochemistry

The sections were stained with hematoxylin and eosin (H&E) and Masson's trichrome, and observed under an optical microscope. The keloid spheroid sections were treated with mouse anti-collagen type I (ab6308; Abcam, Ltd., Cambridge, UK), mouse anti-collagen type III (C7805; Sigma, St. Louis, Mo.), mouse anti-elastin (E4013; Sigma), mouse anti-fibronectin (sc-52331; Santa Cruz Biotechnology), rabbit anti-TGF-β1 (ab9758; Abcam, Cambridge, UK), mouse anti-EGFR (Ab-1; Oncogene Research Products, Calbiochem), rabbit anti-Erk 1/2 (#4370S; Cell Signaling Technology, Beverly, Mass.), and rabbit anti-Smad2/3 complex (#8685S; Cell Signaling Technology), mouse anti-PCNA (DAKO), and goat anti-cytochrome C (SC-8385; Santa Cruz Biotechnology) primary antibodies, reacted overnight at 4° C., and then reacted with a secondary antibody at room temperature for 20 minutes using a Dako Envision™ kit (DAKO, Glostrup, Denmark). Diaminobenzidine/hydrogen peroxidase (DAKO, Carpinteria, Calif.) was used as a chromogen substrate. All slides were stained with Meyer's hematoxylin. The expression levels of TGF-β1, EGFR, Erk 1/2, Smad 2/3, type I and III collagen, elastin, and fibronectin were analyzed in a semi-quantitative manner using MetaMorph® image analysis software (Universal Image Corp., Buckinghamshire, UK). The results are expressed as the mean optical density for six different digital images.

Western Blot

KFs were lysed in a solution containing 50 mM Tris-HCl (pH 7.6), 1% Nonidet P-40 (NP-40), 150 mM NaCl, 0.1 mM zinc acetate, and a protease inhibitor. Concentrations of proteins were determined by a Lowry method (Bio-Rad, Hercules, Calif.), and 30 g of each sample was subjected to sodium dodecyl sulfate-polyacrylamide gel electrophoresis (SDS-PAGE). The proteins on the gel were transferred to a polyvinylidene fluoride membrane, treated with a primary mouse anti-mortalin monoclonal antibody (C1-3) and rabbit anti-β-actin antibody (Sigma, St Louis, Mo.), and then incubated with a horseradish peroxidase (HRP)-conjugated secondary antibody (#7074 or 7076; Cell Signaling Technology). The expression patterns were checked using an ECL detection kit (sc-2004; Santa Cruz Biotechnology), and the expression level of mortalin was developed using enhanced chemiluminescence (Amersham Pharmacia Biotech, Uppsala, Sweden). The mortalin protein was analyzed in a semi-quantitative manner using ImageJ software (National Institutes of Health, Bethesda, Md.).

Immunofluorescence Assay

Keloid tissue sections (n=4) were deparaffinized, dehydrated, blocked with 5% goat serum, treated with a mouse anti-mortalin monoclonal antibody (C1-3) or a rabbit anti-p53 (sc-6243; Santa Cruz Biotechnology) primary antibody, and then reacted overnight at 4° C. Thereafter, the sections were washed with phosphate-buffered saline (PBS), treated with an Alexa Flour 488-conjugated goat anti-mouse IgG (A11001; Invitrogen, Carlsbad, Calif.) or Alexa Flour 633-conjugated goat anti-rabbit IgG (A21070; Invitrogen) secondary antibody, and then reacted at room temperature for 60 minutes. Tissues were mounted on slides using a Vectashield mounting medium containing DAPI (Vector Laboratories, Burlingame, Calif.), and then observed under a confocal microscope (LSM700, Olympus, Center Valley, Pa.).

Terminal Deoxynucleotidyl Transferase dUTP Nick End Labeling (TUNEL) Assay

An apoptotic spheroid population was assessed by a TUNEL assay assay (Gene Ther, 2008. 15(9): p. 635-51). The apoptotic cells were observed in five randomly selected fields, and photographed at magnifications of ×100 and ×400. The expression level of apoptotic spheroids was analyzed in a semi-quantitative manner using MetaMorph® image analysis software. The results are expressed as the mean optical density for five different digital images.

Statistics

The results are expressed as the mean±standard error of the mean (SEM). Data were analyzed using a repeated-measures one-way ANOVA. Two sets of independent sample data were compared using a paired t-test; p-values<0.05 were judged to be indicative of statistically significant difference.

Experimental Results

Mortalin Expression Increased in the Keloid Tissues, Compared to the Normal Tissues.

After hematoxylin and eosin (H&E) staining, the present inventors observed that the keloid tissues had a dense and excessive collagen deposition that extended over the clinical keloid margin into the extra-lesional dermal tissues (FIG. 1A). To determine an expression pattern of the mortalin protein in keloid tissues, immunohistochemical staining was performed (n=5). The immunoreactivity of mortalin was remarkably enhanced in the central and peripheral keloid regions (C and D of FIG. 1B), compared to extra-lesional normal tissues (E of FIG. 1B). The increased expression of mortalin was measured in a semi-quantitative manner using MetaMorph® image analysis software (FIG. 1C). The results showed that the level of the mortalin protein was remarkably higher in the central and transitional regions of keloids (optical densities; 92,446±17,322, and 99,007±19,811, respectively) than in the normal tissues (optical density; 23,005±3,969). The expression levels of the mortalin protein in the keloid tissues was 4.8-fold that of the normal tissues (**p<0.01). The mortalin protein expression was assayed using Western blotting (n=3). As can be seen in FIG. 2A, the expression level of the mortalin protein increased 25-fold in the keloid tissues, compared to the normal dermal tissues.

Also, the mortalin protein expression increased 2.3-fold in activated KFs by TGF-β1 (10 ng/mL) (FIG. 2B).

Construction of Mortalin-Specific shRNA-Expressing Adenovirus and Their Effect on KFs and Keloid Spheroids Based on the fact that the mortalin expression increased in the keloid tissues, the present inventors anticipated that the inhibition of mortalin could be applied to treatment of keloid or hypertrophic scars. Therefore, the present inventors constructed a mortalin-specific shRNA-expressing adenovirus (FIG. 3A), and examined the effect of the adenovirus on KFs and keloid spheroids. As can be seen in FIGS. 3B and 3C, a level of the overexpressed mortalin in the cytosolic and extracellular regions of KFs (FIG. 3B) and primary keloid spheroids (FIG. 3C) was remarkably reduced by treatment with dE1-RGD/GFP/shMot, as observed by immunofluorescence assay.

Mortalin-Specific shRNA-Expressing Adenovirus Decreases Expression of Collagen Type I and III, Elastin, and Fibronectin Protein in Primary Human Keloid Spheroids.

Keloid spheroids derived from active-stage keloid patients (n=3) were cultured, and transduced with either dE1-RGD/GFP/scramble or dE1-RGD/GFP/shMot. The effect of mortalin on the expression of major ECM components of keloids was evaluated histologically. Masson's trichrome staining of keloid sections revealed that a decrease in collagen deposition was observed in spheroids transduced with dE1-RGD/GFP/shMot, compared to the scramble virus (FIG. 4A). Also, a dense and coarse collagen bundle structure was converted into a thin and shallow collagen bundle structure. The image analysis through the immunohistochemical staining also showed that the levels of type I collagen, type III collagen, elastin, and fibronectin were significantly reduced by 12%, 43%, 12%, and 18%, respectively, in the dE1-RGD/GFP/shMot-treated keloid spheroids, compared to the scramble virus-transduced spheroids (**p<0.01 in all cases; FIGS. 4B and 4C). As a result, the data suggested that the expression of the major ECM components such as collagen type I and III, elastin, and fibronectin was remarkably reduced by the inhibition of mortalin expression in the primary keloid spheroids.

Mortalin-Specific shRNA-Expressing Adenovirus Reduces Expression of TGF-β1, EGFR, and Erk 1/2 on Keloid Spheroids.

The present inventors examined whether the dE1-RGD/GFP/shMot reduced the expression of TGF-β1 and EGFR in the keloid spheroids, compared to the dE1-RGD/GFP/scramble. To examine the intracellular effect of the mortalin-specific shRNA-expressing adenovirus, the expression of the Smad 2/3 complex and Erk 1/2 protein was determined. As can be seen in FIG. 4D, it was confirmed that the expression levels of TGF-β1, EGFR, Smad 2/3 complex, and Erk 1/2 protein were remarkably reduced by 52%, 43%, 11%, and 42%, respectively, in the mortalin-specific shRNA-expressing adenovirus-treated keloid spheroids, compared to the scramble virus-transduced spheroids (*p<0.05, **p<0.01; FIGS. 4D and 4E). These results showed that the knockdown of mortalin attenuated an EGF/EGFR signaling pathway and a TGF-β1/Smad pathway, and thus plays an important role in fibrogenesis. Also, the overexpressed mortalin plays an important role in keloid pathogenesis, and thus the inhibition of mortalin expression was able to be a therapeutic target for the treatment of keloid or hypertrophic scars.

Knockdown of Mortalin Decreases PCNA Expression and Induces Apoptosis

Keloid formation is usually considered to result in prolonged cell proliferation and reduced apoptosis. Therefore, the proliferation activity of keloids was examined by proliferating cell nuclear antigen (PCNA) immunohistochemical staining (n=5). As a result, it was confirmed that the expression of the PCNA protein remarkably increased 3.9-fold and 3.2-fold, respectively, in the central and transitional keloids, compared to the normal tissues (FIGS. 5A and 5B). Thereafter, the present inventors examined whether the knockdown of mortalin was able to reduce cell proliferation and induce apoptosis in scramble and mortalin-specific shRNA-expressing adenovirus-transfected keloid spheroids. The image analysis through the immunohistochemical staining showed that the PCNA expression was remarkably reduced by 29% in the dE1-RGD/GFP/shMot-treated keloid spheroids (FIGS. 5C and 5D). To examine whether reduced mortalin expression induced apoptosis, a TUNEL assay and cytochrome-C immunostaining were also carried out. As shown in FIGS. 5C and 5E, TUNEL positivity increased in the dE1-RGD/GFP/shMot-treated keloid spheroids. As shown in FIG. 5C and FIG. 5F, the expression of a cytochrome C protein increased 1.8-fold after transduction with dE1-RGD/GFP/shMot. In addition, as shown in FIG. 8, wild type p53, phospho-p53, p21, and caspase 3 were increased by 2.8-, 8.5-, 3.2-, and 5.7-fold, respectively, in primary keloid fibroblast after transduction with dE1-RGD/GFP/shMot (200 MOI) in comparison with dE1-RGD/GFP/scramble (200 MOI) group. Taken together, it can be seen that the mortalin was able to be a target for keloid treatment because the knockdown of the mortalin protein decreased cell proliferation and induced apoptosis.

Mortalin as p53 Inactivator; Mortalin Interacts with p53 and Knockdown of Mortalin Relocates p53 into the Cell Nucleus in Primary Keloid Spheroids.

As can be seen in FIG. 6, the overexpression of a p53 protein in the KFs and keloid tissues (n=5) was confirmed (FIGS. 6B and 6C), and the localization of p53 was found in the cytoplasm and the nucleus, but most of the p53 was expressed in the cytoplasm. The cytoplasmic accumulation of p53 was particularly prominent in the keloid tissues. The present inventors investigated whether mortalin induced inactivation of p53 functionality by cytoplasmic sequestration. If so, the apoptosis caused by mortalin knockdown was expected to induce the nuclear translocation of the p53 and apoptosis by reactivation of p53. To prove this hypothesis, the present inventors performed an immunofluorescence assay on keloid spheroids. The dE1-RGD/GFP/shMot transduction resulted in significant accumulation of p53 in the nucleus. As shown in FIG. 6D, p53 and mortalin were colocalized in the cytosol of the untreated keloid spheroids. After the keloid spheroids were treated with the mortalin-specific shRNA-expressing adenovirus, mortalin expression was knocked down, and intense nuclear staining for p53 was exhibited. In line with these findings, a time-dependent increase in nuclear p53 level was confirmed by western blot analysis in dE1-RGD/shMot-treated primary keloid fibroblast (FIG. 9). The present inventors anticipated that the nuclear translocation of p53 caused changes in apoptosis activity and cytochrome C secretion. Thus, the scrambled shRNA not targeting human genes was used as the control.

DISCUSSION

Keloids are fibro-proliferative skin lesions that develop by excessive accumulation of ECM components (mainly collagens), invasion into normal tissues, and the like. Increased cell proliferation accounts for the progressive and hypertrophic nature of keloids, correlates with a low rate of apoptosis[5,7,9], which plays an important role in pathological scarring. Therefore, the understanding of the mechanism by which the keloids escape from apoptosis will be useful for development of novel therapeutic strategies, regardless of the keloid pathogenesis caused by increased cell proliferation and excessive collagen deposition.

In the present invention, the data showed that the expression of mortalin and tumor suppressor protein p53 increased in the keloid tissues (especially in the cytosol), compared to the normal tissues. In line with these reports, primary patient keloid fibroblast samples used in the present invention expressed wild type p53 (FIG. 7). Also, mortalin expression remarkably increased after the keloid fibroblasts were treated with TGF-β1 (10 ng/mL). Mortalin (mot-2/mthsp70/PBP74/GRP75) is an essential protein belonging to the Hsp70 family of chaperones, and its overexpression causes cell proliferation and growth[15,16,18,20,21]. Mortalin protects cells from senescence and apoptosis and is overexpressed in cancer cells. However, the function of mortalin in fibrotic diseases such as keloid remains to be solved. In this regard, the mortalin-specific shRNA (dE1-RGD/GFP/shMOT) was constructed, and injected into keloid spheroids in order to test an apoptotic and anti-fibrotic effect. After the dE1-RGD/GFP/shMOT transduction, the expression of the major ECM components was remarkably reduced in the primary keloid spheroids, and mortalin knockdown attenuated the EGF/EGFR signaling pathway and TGF-β1/Smad pathway, which have a role in fibrogenesis.

An excessive amount of ECM was produced in the myofibroblasts due to fibrosis, which results in the onset of keloid or hypertrophic scars. However, there are no reports on mechanisms of potential p53 mutations in hypertrophic scar fibroblasts and apoptosis in keloid and hypertrophic scar fibroblasts. The data of the present invention showed that mortalin knockdown induced the nuclear translocation of p53 and reduced cell proliferation. Also, apoptotic activity, cytochrome release, and TUNEL positivity increased in the dE1-RGD/GFP/shMot-treated keloid spheroids.

Therefore, the present inventors expect the functions of dE1-RGD/GFP/shMot such as increased anti-proliferative, anti-fibrotic and apoptotic activities may be very useful for treatment of keloids or hypertrophic scars.

Although certain embodiments of the present invention have been shown and described, it will be apparent to those skilled in the art that the following examples are merely given herein to describe the present invention more fully, and are not intended to limit the scope of the present invention. Therefore, the technical scope of the present invention is defined in the claims and their equivalents.

REFERENCES

1. Bran G M, Goessler U R, Hormann K, Riedel F, Sadick H. Keloids: current concepts of pathogenesis (review). *Int J Mol Med.* 2009; 24: 283-293.
2. Tuan T L, Nichter L S. The molecular basis of keloid and hypertrophic scar formation. *Molecular Medicine Today.* 1998; 4: 19-24.
3. Shih B, Garside E, McGrouther D A, Bayat A. Molecular dissection of abnormal wound healing processes resulting in keloid disease. *Wound Repair Regen.* 2010; 18: 139-153.

4. Chipev C C, Simman R, Hatch G, et al. Myofibroblast phenotype and apoptosis in keloid and palmar fibroblasts in vitro. *Cell Death Differ.* 2000; 7: 166-176.
5. Luo S, Benathan M, Raffoul W, Panizzon R G, Egloff D V. Abnormal balance between proliferation and apoptotic cell death in fibroblasts derived from keloid lesions. *Plast Reconstr Surg.* 2001; 107: 87-96.
6. Ladin D A, Hou Z, Patel D, et al. p53 and apoptosis alterations in keloids and keloid fibroblasts. *Wound Repair Regen.* 1998; 6: 28-37.
7. Lu F, Gao J, Ogawa R, Hyakusoku H, Ou C. Biological differences between fibroblasts derived from peripheral and central areas of keloid tissues. *Plast Reconstr Surg.* 2007; 120: 625-630.
8. Saed G M, Ladin D, Olson J, et al. Analysis of p53 gene mutations in keloids using polymerase chain reaction-based single-strand conformational polymorphism and DNA sequencing. *Arch Dermatol.* 1998; 134: 963-967.
9. De Felice B, Garbi C, Santoriello M, Santillo A, Wilson R R. Differential apoptosis markers in human keloids and hypertrophic scars fibroblasts. *Mol Cell Biochem.* 2009; 327: 191-201.
10. Liu W, Jiang Y H, Li Y L, et al. [Experimental study on p53 gene mutation in keloid fibroblasts]. *Zhonghua Shao Shang Za Zhi.* 2004; 20: 85-87.
11. Heitzer E, Seidl H, Bambach I, et al. Infrequent p53 gene mutation but UV gradient-like p53 protein positivity in keloids. *Exp Dermatol.* 2012; 21: 277-280.
12. De Felice B, Ciarmiello L F, Mondola P, et al. Differential p63 and p53 expression in human keloid fibroblasts and hypertrophic scar fibroblasts. *DNA Cell Biol.* 2007; 26: 541-547.
13. Woods D B, Vousden K H. Regulation of p53 function. *Exp Cell Res.* 2001; 264: 56-66.
14. Lindenboim L, Bogner C, Stein R. Nuclear proteins acting on mitochondria. *Biochim Biophys Acta.* 2011; 1813: 584-596.
15. Kaul S C, Yaguchi T, Taira K, Reddel R R, Wadhwa R. Overexpressed mortalin (mot-2)/mthsp70/GRP75 and hTERT cooperate to extend the in vitro lifespan of human fibroblasts. *Exp Cell Res.* 2003; 286: 96-101.
16. Wadhwa R, Taira K, Kaul S C. An Hsp70 family chaperone, mortalin/mthsp70/PBP74/Grp75: what, when, and where? *Cell Stress Chaperones.* 2002; 7: 309-316.
17. Wadhwa R, Taira K, Kaul S C. Mortalin: a potential candidate for biotechnology and biomedicine. *Histol Histopathol.* 2002; 17: 1173-1177.
18. Ran Q, Wadhwa R, Kawai R, et al. Extramitochondrial localization of mortalin/mthsp70/PBP74/GRP75. *Biochem Biophys Res Commun.* 2000; 275: 174-179.
19. Kaul S C, Aida S, Yaguchi T, Kaur K, Wadhwa R. Activation of wild type p53 function by its mortalin-binding, cytoplasmically localizing carboxyl terminus peptides. *J Biol Chem.* 2005; 280: 39373-39379.
20. Kaul S C, Taira K, Pereira-Smith O M, Wadhwa R. Mortalin: present and prospective. *Exp Gerontol.* 2002; 37: 1157-1164.
21. Kaul S C, Deocaris C C, Wadhwa R. Three faces of mortalin: a housekeeper, guardian and killer. *Exp Gerontol.* 2007; 42: 263-274.
22. Mihara M, Moll U M. Detection of mitochondrial localization of p53. *Methods Mol Biol.* 2003; 234: 203-209.
23. Saxena N, Katiyar S P, Liu Y, et al. Molecular interactions of Bcl-2 and Bcl-xL with mortalin: identification and functional characterization. *Biosci Rep.* 2013; 33.
24. Deocaris C C, Kaul S C, Wadhwa R. On the brotherhood of the mitochondrial chaperones mortalin and heat shock protein 60. *Cell Stress Chaperones.* 2006; 11: 116-128.
25. Lu W J, Lee N P, Kaul S C, et al. Mortalin-p53 interaction in cancer cells is stress dependent and constitutes a selective target for cancer therapy. *Cell Death Differ.* 2011; 18: 1046-1056.
26. Lu W J, Lee N P, Kaul S C, et al. Induction of mutant p53-dependent apoptosis in human hepatocellular carcinoma by targeting stress protein mortalin. *Int J Cancer.* 2011; 129: 1806-1814.
27. Wadhwa R, Takano S, Taira K, Kaul S C. Reduction in mortalin level by its antisense expression causes senescence-like growth arrest in human immortalized cells. *J Gene Med.* 2004; 6: 439-444.
28. Ryu J, Kaul Z, Yoon A R, et al. Identification and functional characterization of nuclear mortalin in human carcinogenesis. *J Biol Chem.* 2014; 289: 24832-24844.
29. Wu H, Yoon A R, Li F, Yun C O, Mahato R I. RGD peptide-modified adenovirus expressing hepatocyte growth factor and X-linked inhibitor of apoptosis improves islet transplantation. *J Gene Med.* 2011; 13: 658-669.
30. Yoo J Y, Ryu J, Gao R, et al. Tumor suppression by apoptotic and anti-angiogenic effects of mortalin-targeting adeno-oncolytic virus. *J Gene Med.* 2010; 12: 586-595.
31. Yoo J Y, Kim J H, Kim J, et al. Short hairpin RNA-expressing oncolytic adenovirus-mediated inhibition of IL-8: effects on antiangiogenesis and tumor growth inhibition. *Gene Ther.* 2008; 15: 635-651.
32. Yoo J Y, Kim J H, Kwon Y G, et al. VEGF-specific short hairpin RNA-expressing oncolytic adenovirus elicits potent inhibition of angiogenesis and tumor growth. *Mol Ther.* 2007; 15: 295-302.
33. Bellaye P S, Burgy O, Causse S, Garrido C, Bonniaud P. Heat shock proteins in fibrosis and wound healing: good or evil? *Pharmacol Ther.* 2014; 143: 119-132.
34. Cai W F, Zhang X W, Yan H M, et al. Intracellular or extracellular heat shock protein 70 differentially regulates cardiac remodelling in pressure overload mice. *Cardiovasc Res.* 2010; 88: 140-149.
35. Asea A, Rehli M, Kabingu E, et al. Novel signal transduction pathway utilized by extracellular HSP70: role of toll-like receptor (TLR) 2 and TLR4. *J Biol Chem.* 2002; 277: 15028-15034.
36. Lee J H, Shin J U, Jung I, et al. Proteomic profiling reveals upregulated protein expression of hsp70 in keloids. *Biomed Res Int.* 2013; 2013: 621538.
37. Chen J J, Zhao S, Cen Y, et al. Effect of heat shock protein 47 on collagen accumulation in keloid fibroblast cells. *Br J Dermatol.* 2007; 156: 1188-1195.
38. Chen J J, Jin P S, Zhao S, et al. Effect of heat shock protein 47 on collagen synthesis of keloid in vivo. *ANZ J Surg.* 2011; 81: 425-430.
39. Vousden K H, Prives C. Blinded by the Light: The Growing Complexity of p53. *Cell.* 2009; 137: 413-431.
40. Laptenko O, Prives C. Transcriptional regulation by p53: one protein, many possibilities. *Cell Death Differ.* 2006; 13: 951-961.
41. Kaul S C, Duncan E L, Englezou A, et al. Malignant transformation of NIH3T3 cells by overexpression of mot-2 protein. *Oncogene.* 1998; 17: 907-911.
42. Xu J, Xiao H H, Sartorelli A C. Attenuation of the induced differentiation of HL-60 leukemia cells by mitochondrial chaperone HSP70. *Oncol Res.* 1999; 11: 429-435.
43. Ahi Y S, Bangari D S, Mittal S K. Adenoviral vector immunity: its implications and circumvention strategies. *Curr Gene Ther.* 2011; 11: 307-320.

What is claimed is:

1. A method of treating keloid diseases or scars, comprising:
administering a therapeutically effective amount of an inhibitor, which suppresses an expression of a mortalin gene or an activity of a mortalin protein, to a subject in need thereof,
wherein the inhibitor is shRNA, siRNA, miRNA, an antisense oligonucleotide, a ribozyme, a DNAzyme, a peptide nucleic acid, an antibody or an aptamer, and
wherein shRNA, siRNA, miRNA, the antisense oligonucleotide, the ribozyme, the DNAzyme or the peptide nucleic acid comprises a sequence complementary to mRNA or DNA of the mortalin gene and suppresses an expression of the mortalin gene, and the antibody or the aptamer specifically binds to the mortalin protein and suppresses the activity of the mortalin protein.

2. The method of claim 1, wherein the inhibitor is shRNA, siRNA, miRNA, or an antisense oligonucleotide, which suppresses the expression of the mortalin gene.

3. The method of claim 1, wherein the shRNA, siRNA, miRNA or antisense oligonucleotide comprises a sequence complementary to a sequence from 2,102th nucleotide to 2,120th nucleotide of SEQ ID NO: 2.

4. The method of claim 3, wherein the shRNA has a sequence complementary to a nucleotide sequence of SEQ ID NO: 1.

5. The method of claim 4, wherein the shRNA comprises a sequence of SEQ ID NO: 3 or SEQ ID NO: 4.

6. The method of claim 1, wherein the keloid diseases or scars is postoperative scars, burn keloids, keloids, posttraumatic keloids, restenosis after percutaneous coronary angioplasty, or hypertrophic scar pannus.

7. A method of treating keloid diseases or scars, comprising:
   administering, to a subject in need thereof, a pharmaceutical composition, which comprises:
   (a) a therapeutically effective amount of an adenovirus expressing an oligonucleotide for inhibiting an expression of a mortalin gene as an active ingredient; and
   (b) a pharmaceutically acceptable carrier.

8. The method of claim 7, wherein the adenovirus is a recombinant adenovirus comprising the following sequences:
   (a) an inverted terminal repeat (ITR) sequence of the adenovirus;
   (b) an oligonucleotide sequence for inhibiting the expression of a mortalin gene, which comprises a sequence complementary to a sequence from 2,102th nucleotide to 2,120th nucleotide of SEQ ID NO:2; and
   (c) a promoter sequence located downstream of the oligonucleotide sequence.

* * * * *